United States Patent
Nguyen Duy et al.

(10) Patent No.: US 12,093,796 B2
(45) Date of Patent: Sep. 17, 2024

(54) METHOD FOR DETERMINING MECHANICAL PROPERTIES OF A ROLLED MATERIAL USING A HYBRID MODEL

(71) Applicant: Primetals Technologies Austria GmbH, Linz (AT)

(72) Inventors: Du Nguyen Duy, Hagenberg im Mühlkreis (AT); Katharina Freinschlag, Klam (AT); Sergey Bragin, Linz (AT); Klaus Jax, Hellmonsödt (AT); Axel Rimnac, Linz (AT); Alfred Seyr, Oberschlierbach (AT); Sonja Strasser, Garsten (AT)

(73) Assignee: Primetals Technologies Austria GmbH, Linz (AT)

( * ) Notice: Subject to any disclaimer, the term of this patent is extended or adjusted under 35 U.S.C. 154(b) by 0 days.

(21) Appl. No.: 18/293,067

(22) PCT Filed: Jul. 13, 2022

(86) PCT No.: PCT/EP2022/069634
§ 371 (c)(1),
(2) Date: Jan. 29, 2024

(87) PCT Pub. No.: WO2023/006430
PCT Pub. Date: Feb. 2, 2023

(65) Prior Publication Data
US 2024/0265302 A1    Aug. 8, 2024

(30) Foreign Application Priority Data

Jul. 27, 2021    (EP) .................................... 21187849

(51) Int. Cl.
*G06N 20/00*    (2019.01)
*B21B 37/00*    (2006.01)
*G06F 30/27*    (2020.01)

(52) U.S. Cl.
CPC ............. *G06N 20/00* (2019.01); *B21B 37/00* (2013.01); *G06F 30/27* (2020.01)

(58) Field of Classification Search
CPC .......... G06N 20/00; G06F 30/27; B21B 37/00
See application file for complete search history.

(56) References Cited

U.S. PATENT DOCUMENTS 3,694,636 A * 9/1972 Smith, Jr. ............... B21B 37/16
                                                              72/11.8
3,713,313 A * 1/1973 Spradlin ................. B21B 37/16
                                                              72/10.4

(Continued)

FOREIGN PATENT DOCUMENTS

CN        101046682 A        10/2007
CN        107609647 A1        1/2018

(Continued)

OTHER PUBLICATIONS

A. K. Pani and H. K. Mohanta, "A hybrid soft sensing approach of a cement mill using principal component analysis and artificial neural networks," 2013 3rd IEEE International Advance Computing Conference (IACC), Ghaziabad, India, 2013, pp. 713-718, doi: 10.1109/IAdCC.2013.6514314. (Year: 2013).*

(Continued)

*Primary Examiner* — Charles L Beard
(74) *Attorney, Agent, or Firm* — Liang & Hennessey LLP; Brian Hennessey

(57) ABSTRACT

A method for determining mechanical properties of a first rolled material by a hybrid model that includes production datasets relating to further rolled materials, a physical production model and a statistical data model. The production dataset relating to the first rolled material is used to determine a first mechanical dataset, a further production dataset and a metallurgical dataset and also a second mechanical dataset. An averaged normalized distance value for produc- (Continued)

tion datasets relating to the further rolled materials is determined that is used to ascertain the mechanical properties of the rolled material as a weighted average from the first and second mechanical datasets. When creating the hybrid model, the physical production model is used to determine further production datasets relating to the further rolled goods for training the statistical data model.

15 Claims, 4 Drawing Sheets

(56) References Cited

U.S. PATENT DOCUMENTS

| | | | | |
|---|---|---|---|---|
| 5,357,443 | A * | 10/1994 | Watanbe | G01N 33/204 |
| | | | | 148/541 |
| 5,386,945 | A * | 2/1995 | Nose | B02C 25/00 |
| | | | | 241/34 |
| 5,461,894 | A * | 10/1995 | Sorgel | B21B 37/16 |
| | | | | 700/148 |
| 5,513,097 | A * | 4/1996 | Gramckow | G05B 13/027 |
| | | | | 706/903 |
| 5,673,368 | A * | 9/1997 | Broese | B21B 37/74 |
| | | | | 706/903 |
| 5,797,288 | A * | 8/1998 | Mas | B21B 37/00 |
| | | | | 72/7.1 |
| 5,860,304 | A * | 1/1999 | Anbe | B21B 37/28 |
| | | | | 72/11.8 |
| 5,966,682 | A * | 10/1999 | Gramckow | G05B 17/02 |
| | | | | 702/170 |
| 6,024,808 | A * | 2/2000 | Kondo | C21D 8/10 |
| | | | | 148/547 |
| 6,225,609 | B1 * | 5/2001 | Imanari | C21D 9/573 |
| | | | | 219/486 |
| 6,340,108 | B1 * | 1/2002 | Isoyama | B23K 20/028 |
| | | | | 228/103 |
| 6,430,461 | B1 * | 8/2002 | Andorfer | B21B 37/00 |
| | | | | 700/148 |
| 6,473,658 | B1 * | 10/2002 | Brose | B21B 37/00 |
| | | | | 700/44 |
| 6,529,780 | B1 * | 3/2003 | Soergel | G05B 13/027 |
| | | | | 700/19 |
| 6,691,540 | B2 * | 2/2004 | Hohne | B21B 37/28 |
| | | | | 700/149 |
| 6,782,304 | B1 * | 8/2004 | Tsugeno | G05B 13/0265 |
| | | | | 700/89 |
| 6,842,656 | B1 * | 1/2005 | Burkhardt | B21B 37/00 |
| | | | | 700/109 |
| 6,866,729 | B2 * | 3/2005 | Gramckow | C21D 9/573 |
| | | | | 266/87 |
| 6,948,347 | B2 * | 9/2005 | Russo | G01B 7/345 |
| | | | | 700/154 |
| 7,251,971 | B2 * | 8/2007 | Reinschke | B21B 37/74 |
| | | | | 72/8.5 |
| 7,310,981 | B2 * | 12/2007 | Kurz | C21D 11/00 |
| | | | | 700/148 |
| 8,108,064 | B2 * | 1/2012 | Mukhopadhyay | B21B 38/00 |
| | | | | 700/148 |
| 8,150,544 | B2 * | 4/2012 | Burvenich | G05B 13/021 |
| | | | | 700/71 |
| 8,935,945 | B2 * | 1/2015 | Shimoda | B21B 37/74 |
| | | | | 72/12.2 |
| 11,319,611 | B2 * | 5/2022 | Biglari | G01N 23/2055 |
| 11,731,317 | B1 * | 8/2023 | Stewart | G05B 23/0297 |
| | | | | 156/64 |
| 2004/0167759 | A1 * | 8/2004 | Kawakami | G06F 30/20 |
| | | | | 703/6 |
| 2005/0125091 | A1 * | 6/2005 | Reinschke | B21B 37/28 |
| | | | | 700/148 |
| 2005/0273299 | A1 * | 12/2005 | Toyosawa | G06F 30/20 |
| | | | | 703/7 |
| 2006/0074613 | A1 * | 4/2006 | Oyama | B65H 5/062 |
| | | | | 703/2 |
| 2006/0074615 | A1 * | 4/2006 | Sugiyama | B65H 7/00 |
| | | | | 703/6 |
| 2007/0151635 | A1 * | 7/2007 | Sano | B21B 37/44 |
| | | | | 148/508 |
| 2009/0235707 | A1 * | 9/2009 | Schmidt | B21B 37/00 |
| | | | | 72/11.1 |
| 2009/0282884 | A1 * | 11/2009 | Pawelski | B21B 37/44 |
| | | | | 72/201 |
| 2010/0100218 | A1 * | 4/2010 | Weinzierl | G05B 17/02 |
| | | | | 700/104 |
| 2010/0299082 | A1 * | 11/2010 | Toyosawa | G06F 30/20 |
| | | | | 702/33 |
| 2010/0326155 | A1 * | 12/2010 | Felkl | B21B 37/16 |
| | | | | 72/12.7 |
| 2011/0103426 | A1 * | 5/2011 | Narihara | B21C 51/00 |
| | | | | 266/44 |
| 2011/0106512 | A1 * | 5/2011 | Hainke | G05B 17/02 |
| | | | | 703/2 |
| 2012/0004757 | A1 * | 1/2012 | Imanari | B21B 37/74 |
| | | | | 700/104 |
| 2013/0030561 | A1 * | 1/2013 | Imanari | B21B 37/76 |
| | | | | 700/153 |
| 2013/0098127 | A1 * | 4/2013 | Isei | B21B 1/22 |
| | | | | 72/17.3 |
| 2014/0129023 | A1 * | 5/2014 | Dagner | G05B 15/02 |
| | | | | 700/148 |
| 2016/0016212 | A1 * | 1/2016 | Charre | B21B 1/22 |
| | | | | 72/41 |
| 2016/0076119 | A1 * | 3/2016 | Linzer | C21D 1/54 |
| | | | | 148/503 |
| 2016/0101450 | A1 * | 4/2016 | Linzer | B21B 37/76 |
| | | | | 72/251 |
| 2016/0180269 | A1 * | 6/2016 | Shimoda | G06Q 50/06 |
| | | | | 705/7.22 |
| 2018/0260717 | A1 * | 9/2018 | Li | G06N 5/022 |
| 2019/0302710 | A1 * | 10/2019 | Neti | G06N 20/00 |
| 2019/0361409 | A1 * | 11/2019 | Bettinger | G05B 13/0265 |
| 2020/0024712 | A1 * | 1/2020 | Iwamura | B22D 2/006 |
| 2020/0047230 | A1 * | 2/2020 | Opitz | B21B 45/0218 |
| 2020/0209840 | A1 * | 7/2020 | Ryu | G05B 13/048 |
| 2021/0149381 | A1 * | 5/2021 | Hatakenaka | G05B 19/41885 |
| 2021/0245214 | A1 * | 8/2021 | Fischer | B21B 27/10 |
| 2021/0279610 | A1 * | 9/2021 | Hatakenaka | G05B 19/188 |
| 2021/0365008 | A1 * | 11/2021 | Park | B21B 37/00 |
| 2022/0088654 | A1 * | 3/2022 | Rimnac | C21D 1/60 |
| 2022/0126342 | A1 * | 4/2022 | Sugiyama | G06N 3/08 |
| 2022/0187847 | A1 * | 6/2022 | Cella | G06Q 10/06375 |
| 2022/0236725 | A1 * | 7/2022 | Imanari | G05B 13/0265 |
| 2022/0236728 | A1 * | 7/2022 | Deodhar | G05B 23/0294 |
| 2022/0355356 | A1 * | 11/2022 | Bergmann | B21B 38/006 |
| 2022/0390888 | A1 * | 12/2022 | Onaka | G03G 15/5029 |
| 2023/0001473 | A1 * | 1/2023 | Houshuyama | B22D 11/126 |
| 2023/0118015 | A1 * | 4/2023 | Lindgren | B21B 38/02 |
| | | | | 72/9.1 |
| 2023/0321706 | A1 * | 10/2023 | Ojima | G06Q 50/04 |
| | | | | 29/407.01 |
| 2023/0393113 | A1 * | 12/2023 | Matsushita | G05B 13/0265 |
| 2024/0033797 | A1 * | 2/2024 | Fujita | B21B 37/007 |
| 2024/0091833 | A1 * | 3/2024 | Fujita | B21B 37/007 |
| 2024/0149317 | A1 * | 5/2024 | Fujita | B21B 37/00 |
| 2024/0159665 | A1 * | 5/2024 | Shahan | G01N 21/3563 |

FOREIGN PATENT DOCUMENTS

| | | |
|---|---|---|
| JP | 2005315703 A | 11/2005 |
| JP | 2010172962 A | 8/2010 |
| JP | 2011220708 A | 11/2011 |
| WO | 9818970 A1 | 5/1998 |

OTHER PUBLICATIONS

H. Fernandes, A. Halim and W. Wahab, "Modeling Vertical Roller Mill Raw Meal Residue by Implementing Neural Network," 2019 IEEE International Conference on Innovative Research and Devel-

(56) References Cited

OTHER PUBLICATIONS opment (ICIRD), Jakarta, Indonesia, 2019, pp. 1-6, doi: 10.1109/ICIRD47319.2019.9074747. (Year: 2019).*

Z. Wan, X. Wang and J. Wu, "Model Adaptive Learning for Steel Rolling Mill Control," 2008 IEEE International Symposium on Knowledge Acquisition and Modeling Workshop, Wuhan, China, 2008, pp. 903-906, doi: 10.1109/KAMW.2008.4810638. (Year: 2008).*

International Search Report and Written Opinion received in International Application No. PCT/EP2022/069634 dated Oct. 21, 2022, 16 pages.

European Search Report received in European Application No. 21187849.1 dated Jan. 21, 2022, 5 pages.

* cited by examiner

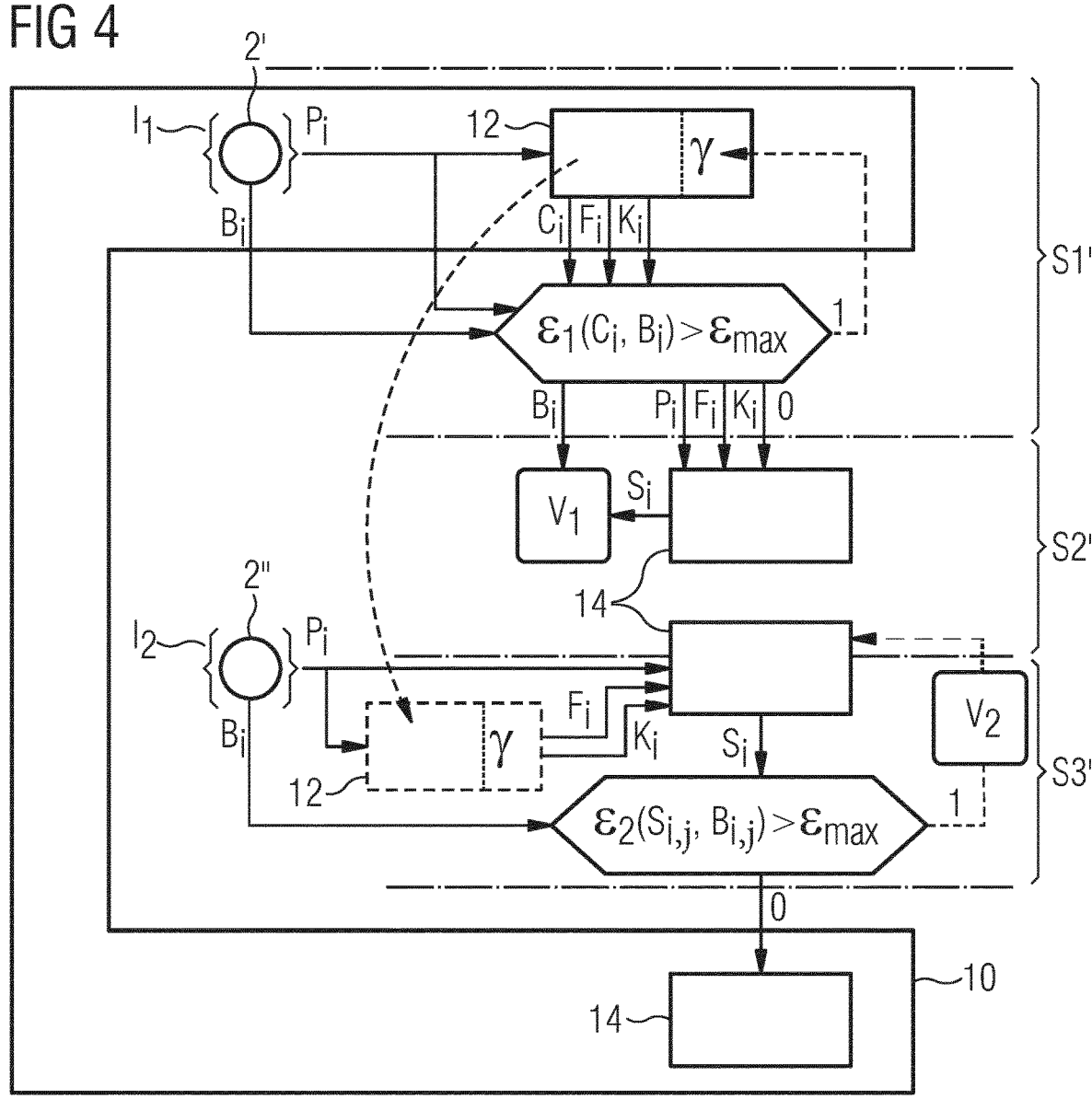

METHOD FOR DETERMINING MECHANICAL PROPERTIES OF A ROLLED MATERIAL USING A HYBRID MODEL

CROSS-REFERENCE TO RELATED APPLICATIONS

The present application is a national phase application of PCT Application No. PCT/EP2022/069634, filed Jul. 13, 2022, entitled "METHOD FOR DETERMINING MECHANICAL PROPERTIES OF A ROLLED MATERIAL USING A HYBRID MODEL", which claims the benefit of European Patent Application No. 21187849.1, filed Jul. 27, 2021, each of which is incorporated by reference in its entirety.

BACKGROUND OF THE INVENTION

1. Field of the Invention

The invention relates to a method for determining mechanical properties of a rolled material using a hybrid model comprising a physical production model and a statistical data model. The invention further relates to a method for creating a hybrid model comprising a physical production model and a statistical data model.

2. Description of the Related Art

In a rolling installation, a metallic rolled material, such as a steel strip, is rolled to reduce its thickness. Furthermore, during and after the rolling process, the rolled material is usually subjected to multiple cooling processes, the cooling being able to be active, for example by applying cooling liquid, or passive, by radiating heat to the surroundings or conducting heat to a surrounding medium (air or transport rollers). Both the reduction in the thickness of the rolled material in the individual rolling passes on passage through the rolling installation and the time-based temperature response of the rolled material in that process and in a subsequent cooling process significantly influence the mechanical properties such as tensile strength $Y_s$, yield strength $T_s$ or elongation at break $A_1$ of the rolled material produced. In order therefore to ensure that the mechanical properties of a rolled material that is produced have certain specified values, sampling, i.e. taking a sample from the rolled material in question and measuring its mechanical properties, is usually necessary.

The sampling of rolled material, for example steel strip, is accordingly complex, which is why attempts are made to avoid it to a large extent and to replace it with a computation of the mechanical properties instead. For this purpose, the prior art involves the use of physical or metallurgical models that allow the evolution of various material properties of a rolled material over time during the production process to be simulated by computer and from which the desired mechanical properties can be derived.

For example, CN101046682 (A) discloses a method in which the temperature response of hot-rolled metal strips is modeled during their production in a roughing line, in a finishing rolling line and in a cooling section, and metallurgical properties of the metal strips are ascertained, from which the tensile strength $Y_s$, the yield strength $T_s$ or the elongation at break $A_1$ of the metal strips are ascertained on the basis of empirical formulae.

Furthermore, so-called statistical data models are used to attempt to ascertain correlations between, for example, the chemical composition and/or process parameters recorded during the production of a rolled material, on the one hand, and the mechanical properties of the rolled material, on the other. In this case, the chemical composition or process parameters form the so-called input variables of a statistical model, while the mechanical properties represent its so-called output variables.

An appropriate statistical data model is usually created for a production installation by relating the input variables of certain rolled products produced on the installation to the output variables recorded in respective samplings, which is also referred to as 'training' the statistical data model or 'machine learning'. The input and output variables of the rolled products used to train the statistical data model are also referred to as so-called 'training datasets'. The totality of the output variables of the test datasets is also referred to as the 'solution space' of the statistical data model.

In order to check the validity of the trained statistical data model, it is usually validated by subjecting further rolled products produced on the same installation to sampling and comparing the values ascertained as so-called 'target variables' with the output variables (in line with the forecast values) of the trained statistical data model. The input and target variables of the further rolled products used for validating the statistical data model are referred to as so-called 'test datasets'.

A statistical data model trained and validated in such a way can therefore be used to take the input variables (e.g. chemical composition, production parameters) of further rolled products produced on the same installation and to ascertain their output variables (mechanical properties) without corresponding physical sampling. Statistical data models can be in the form, for example, of artificial neural networks or of random forest models.

CN107609647 (A) discloses a method for generating a statistical data model for predicting mechanical properties of rolled products made of different alloy constituents and different heat treatments on the basis of a neural network, wherein the mechanical properties for a number of rolled products are ascertained using a mechanical test method in the form of training datasets and test datasets, and wherein the neural network is trained using the training datasets and evaluated on the basis of the test datasets.

JP 2005-315703 (A) discloses a method in which metallurgical properties, for example the metallurgical phase fractions and grain sizes formed during the production process, are first determined for hot-rolled steel strips using a metallurgical model and, together with the chemical composition and the production parameters of the metal products, are supplied to a neural network as input variables, said neural network then being used to ascertain mechanical properties of the metal products, such as tensile strength $Y_s$, yield strength $T_s$ or elongation at break $A_1$, and ductile-brittle transition temperature.

US 2018/0260717 A1 discloses a method for predicting mechanical properties of microalloyed steel, wherein a first step involves ascertaining independent influencing factors of the mechanical properties on the basis of a random forest model, a second step involves modeling the formation of carbonitrides on the basis of a thermodynamic phase model during the rolling process, a third step involves presenting the mechanical properties as the sum of individual empirical-metallurgical submodels of the independent variables, a fourth step involves parameterizing the submodels by means of a back propagation algorithm and a fifth step involves verifying the submodels on the basis of plausibility considerations and production data.

In principle, a statistical data model can ascertain reliable output variables only from such input variables as can be recorded with acceptable accuracy and reproducibility. Therefore, the methods known from the prior art that use statistical data models have disadvantages because they do not take into account some process parameters relevant to the sought mechanical properties of rolled material during production thereof: in a cooling section of a hot rolling installation, for example, water vapor formation and water coatings on the rolled material can severely interfere with a temperature measurement, meaning that missing or invalid measured values have to be replaced with estimates. As a result, a valid recording of the corresponding cooling rate as an input variable for a statistical data model is not possible without modeling the production process, the cooling rate being an important influencing factor for the form of the metallurgical microstructure and therefore the mechanical properties of the rolled material, however.

A disadvantage of the statistical data models known from the prior art is also that the validity of the predicted output variables is, strictly speaking, limited to the location of the sampling. However, since sampling is usually performed only at one point on the rolled material, the effects of production-related fluctuations in the process parameters over the length of a rolled material are not recorded. Especially in the case of rolled strips wound into coils, sampling is carried out near the end of the respective strip for reasons of accessibility.

Furthermore, a statistical data model can make valid statements only within its solution space, while outside this solution space the results are not trustworthy. The accuracy of the results is also limited in scant areas of the input variables of a statistical data model, in which only a small number of training datasets are available. In other words, this means that a statistical data model can make valid statements only in those areas of the input variables in which there are a sufficient number of datasets of appropriate quality during training, and so a statistical data model cannot make a valid statement if a process dataset of a rolled material whose mechanical properties are to be predicted is far outside the range defined by the input variables of the training datasets of the relevant statistical data model.

For these reasons, the extrapolation capability of statistical data models is low in practice, since although the available datasets for training the models are extensive, they only contain a certain number of rolled material grades and only map certain modes of production on a specific installation. Rounded measured values in the training datasets can also cause additional problems.

SUMMARY OF THE INVENTION

The invention is based on the object of overcoming the disadvantages of the methods known from the prior art.

The object is achieved according to the invention by a method for determining mechanical properties of a rolled material using a hybrid model, the hybrid model comprising a physical production model and a statistical data model, having the features of claim 1. Furthermore, the object is achieved by a method for creating a hybrid model having the features of claim 9. The dependent claims relate to advantageous embodiments of the invention.

The method according to the invention for determining mechanical properties of a rolled material produced in a rolling mill involves taking a production dataset $P_f$ of a first rolled material as a basis for determining mechanical properties $J_f$ of the first rolled material using a hybrid model. The rolling mill may be a hot rolling mill in particular.

The hybrid model comprises production datasets $P_i$ of further rolled materials produced in the rolling mill, a physical production model and a trained and validated statistical data model. The further rolled materials form a first set $I_1$ of rolled materials produced in the rolling mill. For each of the production datasets $P_i$ of the further rolled materials there is a respective corresponding sampling dataset $B_i$ available that comprises the mechanical properties of the further rolled material ascertained by means of a sampling device after production of the relevant further rolled material in the rolling mill. However, the sampling datasets $B_i$ of the further rolled materials are not themselves part of the hybrid model, but are only used to create it. In short, this means that all of the further rolled materials produced in the rolling mill have been sampled and their mechanical properties recorded.

The production datasets $P_i$ of the further rolled materials have already been supplied to the statistical data model as input variables in the course of its creation in the form of training datasets in the sense defined above. After validation, the predictive properties of the statistical data model are not modified again after its last 'training'.

The data of the production dataset $P_f$ of the first rolled material and the production datasets $P_i$ of the further rolled materials are recorded in—or, viewed from the point of view of time, during—the production of the respective rolled material in the rolling mill. Accordingly, individual or all data of a production dataset can be time-dependent, in which case the applicable time-dependent data each comprise multiple data values from different times during the production process.

A production dataset $P_f$ of the first rolled material or the further rolled materials $P_i$ comprises, in each case, only such data as can either be recorded by measuring means (for example from a temperature measurement or a speed measurement on the rolled material concerned) or as can be specified by automation means or by an operator. These are thus manipulated or measured variables that can be recorded and stored by data processing means, for example by an installation automation system before or during production of the applicable rolled materials in the rolling mill, and can comprise data that are already known before the start of production of the respective rolled material: for example it is possible for foreign element fractions, setup values for units of the rolling mill or an initial thickness of a rolled material on entering the rolling mill to be specified by a higher-level control system or manually by an operator. In other words, the production dataset $P_f$ of the first rolled material or the production datasets $P_i$ comprise data that influence the production process for the rolled material in question.

The physical production model for modeling the production process for a rolled material produced in the rolling mill comprises a set of metallurgical model parameters, which are subsumed below under the symbol $\gamma$. These metallurgical model parameters $\gamma$ represent, within the scope of the invention, physical influencing variables, the values of which are chosen within plausible limits and which can be used to carry out the modeling of the production process in good approximation to the actual production process taking place.

The physical production model with the metallurgical model parameters $\gamma$ can be used to ascertain a first mechanical dataset $C_f$ of the first rolled material from the production dataset $P_f$ of the first rolled material, a further production dataset $F_f$ of the first rolled material, comprising further production data of the first rolled material during production thereof in the rolling mill, and a metallurgical dataset Kr of the first rolled material, comprising metallurgical properties of the first rolled material during production thereof in the rolling mill. The expression 'during production' refers to a period of time between the start of production and the completion of the production process for the first rolled material on the rolling installation.

The first mechanical dataset $C_f$, the further production dataset $F_f$ and the metallurgical dataset $K_f$ are ascertained in the form of a modeling, i.e. the production process for the first rolled material is recreated by computer on the basis of the physical production model based on physical equations and based on empirical equations using the metallurgical model parameters γ, meaning that the data of the mechanical dataset $C_f$, of the further production dataset $F_f$ and of the metallurgical dataset Kr are each explicitly dependent on the metallurgical model parameters γ in mathematical terms.

The first mechanical dataset $C_f$ comprises the mechanical properties of the first rolled material after production thereof in the rolling mill. The expression 'after production' refers to a period during which production of the rolled material in question in the rolling mill has finished and further processing steps (for example sampling of the rolled material or transport to a further-processing installation) can be carried out.

The physical equations used for the physical production model can be, for example, a heat conduction equation in consideration of appropriate boundary conditions and in conjunction with a coupled system of equations for the phase fractions of a rolled material.

For example, such equations are known—with particular regard to carbon diffusion between individual metallurgical phases—from Wolff et al., Archives of Mechanics, 59, 4-5, pp. 435-466, 2007: in this, (2.27) represents a heat conduction equation for steel in which, in addition to the austenitic phase, further metallurgical phases and the released latent heat are taken into account when the austenitic phase is transferred to the further phases. Furthermore, (2.41) represents a coupled system of equations for the transformation of the individual metallurgical phases into each other, into which system the transition rates between individual phases are entered as metallurgical model parameters. Expressions (2.30) and (2.31) represent the initial condition or boundary condition for the thermal conduction equation. The specific heat capacity and the thermal conductivity of the steel and also the thermal conductivity coefficient of the boundary condition each depend on the proportion of the individual metallurgical phases in the steel.

An alternative form of the thermal conduction equation is $$\frac{\partial}{\partial t} \sum_{k=1}^{m} p_k h_k - \frac{\partial}{\partial x}\left[\frac{\lambda(h, p_1, \ldots, p_m)}{\rho} \frac{\partial T(h, p_1, \ldots, p_m)}{\partial x}\right] = s \quad (1)$$

In equation (1), $p_k$ with k=1, . . . ,m are phase fractions of the rolled material, for example an austenite fraction, a ferrite fraction, a cementite fraction and/or other proportions. The phase fractions are always non-negative and add up to one. The thermal conductivity λ in this instance is also expressed as a function dependent on the enthalpy density h and the phase fractions $p_k$. The variable ρ denotes the density of the rolled material, which is assumed to be the same for all phase fractions. The variable s denotes a heat source term that arises when the rolled material passes through a roll gap, said term being proportional to the yield stress of the rolled piece formed in the roll gap. The heat source term can be ascertained in a known manner if the roll gap geometry and the rolling speed are known.

The variable h is an enthalpy density of the rolled material under consideration, where $$h = \sum_{k=1}^{m} p_k h_k \quad (2)$$

applies. Furthermore, known dependencies exist, for each phase fraction $p_k$, between the enthalpy density fraction $h_k$ of the respective phase fraction and the associated temperature $T_k$, i.e. the temperature $T_k=T_k(h_k)$ is a strictly monotonously rising function of the enthalpy density fraction $h_k$. The relationship $$T_1(h_1)=T_2(h_2)= \ldots =T_m(h_m)=T \quad (3)$$

applies because the temperature at one point can only assume a single value, which is the same for all phase fractions $p_k$. For the change in the phase fractions $p_k$ over time (phase conversion equations), it is in turn possible to represent a coupled differential equation system in the form $$\frac{dp_k}{dt} = f_{pk}(T, p_1, \ldots, p_m), k = 1, \ldots, m \quad (4)$$

using model functions $f_{pk}(T, p_1, \ldots, p_m)$ that describe the conversion and growth kinetics of individual metallurgical phases $p_k$. Such model functions can be used as so-called Jonson-Mehl-Avrami equations (for example from Buchmayr, Materials and Production Engineering using Mathcad, ISBN 3-540-43014-8 Springer-Verlag 2002, chap. 3.4.2, p. 87); similar systems of equations for models of phase transformations in steel are also known from Wolff/Boettcher/Boehm, Phase transformations in steel in the multi-phase case—general modelling and parameter identification, Report 07-02, University of Bremen (https://www.researchgate.net/publication/237220674_Phase_transformation_in_steel_in_the_multi-phase_case_-_general_modelling_and_parameter_identification): such systems of equations for their part contain metallurgical model parameters such as a time exponent or a nucleation rate, the values of which must be assumed within plausible limits.

As a boundary condition for the heat conduction equation (1), a heat flux density $j_o$ is usually specified for the surface of the rolled material, to whose volume equations (1) to (4) refer: this heat flux density $j_o$ describes the heat flux that is exchanged from the rolled material, via the surface thereof, with the surroundings of the rolled material (e.g. ambient air, coolant applied to the rolled material, or rolls or rollers making contact with the rolled material); the heat flux density $j_o$ can be modeled, for example, as $$j_o(T_o)=\varepsilon_s(T_o^4-T_u^4)+\alpha v^{0.4}(T_o-T_1)+\beta(T_o-T_r) \quad (5)$$

In equation (5), the first, second and third terms describe a radiation exchange with the surroundings, a convective heat exchange with the ambient air or a heat conduction process with a roller or roll making contact with the rolled material. Here, $T_o$ corresponds to the surface temperature of the rolled material, $T_u$ to the ambient temperature relevant to the radiation exchange, α to a heat transfer coefficient between the rolled material and the ambient air, $T_1$ to the temperature of the ambient air, v to a transport speed of the rolled material relative to the ambient air, β to a heat conduction coefficient to a roller or roll and $T_r$ to the temperature of the relevant roller or roll. In turn, plausible values must be assumed for the variables $\varepsilon_s$, $\alpha$, $\beta$ and, if applicable, for $T_u$, $T_1$ and $T_r$ in the context of modeling the rolling process; these variables therefore represent further model parameters of the physical production model, which, however, do not belong to the aforementioned metallurgical model parameters $\gamma$.

By collectively solving the equations specified by (1) to (4) it is possible—on the basis of an assumed initial value distribution for the temperature or enthalpy $T(h^0, p_1^0, \ldots, p_m^0)$ and initial value distribution of the individual phase fractions $p_k^0$ and taking into account applicable boundary conditions for the thermal conduction equation (1) such as equation (5)—to ascertain the temperature or enthalpy distribution $T(h, p_1, \ldots, p_m)$ that results after a certain period.

For example, the initial value distributions can refer to a time shortly before the rolled material in question enters the rolling mill at which the rolled material usually has a high and evenly distributed temperature and, if necessary, consists of only a few metallurgical phases—for example only a single austenitic phase. For example, the period of time for which equations (1) to (4) are solved may extend to the time interval corresponding to the production time for the rolled material in the rolling mill up until coiling, whereby the entire production process in the rolling mill is modeled by computer.

Alternatively, equations (1) to (4) can each be solved for multiple time intervals immediately following each other, with equations (1) to (4) differing in each time interval. The results at the end of a period of time represent the initial values for the immediately following period of time. As a result, only one part of the production process in the rolling mill is mapped in each time interval. As a result of this approach, the computational modeling of the production process can be adapted particularly well to the respective production section in the rolling mill by way of appropriate selection, for example, of the heat conduction equation or the phase conversion equations.

Furthermore, to ascertain mechanical properties of a rolled material, it is known, for example from Buchmayr, Materials and Production Technology using Mathcad, ISBN 3-540-43014-8 Springer-Verlag 2002, chap. 3.9.2.1-3.9.2.4, pp. 122-123, how the yield strength $T_s$ of the rolled material changes depending on foreign element fractions in the rolled material or under the mechanisms of mixed crystal consolidation, cold hardening, fine grain hardening on the basis of the Hall-Petch relationship or particle hardening. These mechanisms are described in the form of empirical metallurgical equations in which certain variables can each be varied within a certain value range. These variables include, for example, a proportionality constant during mixed crystal hardening, a further proportionality constant or a grain diameter during fine grain hardening, a solidification exponent during cold hardening or a particle size during particle hardening, and also represent metallurgical model parameters of the physical production model. For example, Ibabe, Thin Slab Direct Rolling of Microalloyed Steels, ISBN 0-87849-485-5, Volume 33 of Materials Science Foundations (ISSN 1422-3597), discloses the practice of using an empirical equation (Eq. 44 p. 70) to determine a ferrite grain size from an averaged cooling rate.

Furthermore, the tensile strength $Y_s$ or the yield strength $T_s$ of a certain phase h of a rolled material can each be expressed, for example, as the sum of a basic contribution $Y_{s,h,0}$ or $T_{s,h,0}$ of the phase h and the contributions $f_{Y,h,i}(c_i)$ and $f_{T,h,i}(c_i)$ of individual foreign element fractions $c_i$ in the relevant phase h:

$$Y_{s,h} = Y_{s,h,0} + \Sigma_i f_{Y,h,i}(c_i) \tag{6}$$

or $$T_{s,h} = T_{s,h,0} + \Sigma_i f_{T,h,i}(c_i) \tag{7}$$

The contributions $f_{Y,h,i}(c_i)$ and $f_{T,h,i}(c_i)$ each denote monotonously rising functions that depend on the foreign element fraction $c_i$ in the phase h. For example, the contribution of perlite to the tensile strength of a rolled material $Y_{S,P}$ in a basic contribution due to the lamellar spacing within the perlite and in a proportion linearly dependent on the carbon content $c_P$ in the perlite can be expressed as $$Y_{S,P} = \frac{\beta}{\sqrt{s_0}} + \alpha_c \cdot c_P \tag{8}$$

In this case, $\alpha_C$ and $\beta$ each denote a metallurgical model parameter specific to perlite, which must be selected or adapted within the framework of a specific model, while $S_0$ represents a known morphological characteristic of perlite.

The tensile strength of a material consisting of a mixture of multiple different phases h can be ascertained, for example, on the basis of the formula $$Y_{S,total} = \sqrt[n]{\frac{\sum_h (x_h)^n \cdot Y_{S,h}}{\sum_h (x_h)^n}} \tag{9}$$

where n, in turn, is a metallurgical model parameter to be selected or adapted within a specific model. Equations (6) to (9) are thus examples of the aforementioned empirical metallurgical equations.

In particular, the timing of the production process or the evolution of properties of the first rolled material over time during production thereof can be represented by modeling. In particular, it is possible to represent the evolution of properties of individual sections of the first rolled material over time, so that the influence of changing production conditions on the mechanical properties of the rolled material can be taken into account.

For example, changing speeds of the first rolled material on passage through the rolling mill, non-constant cooling rates of cooling devices over time or a non-constant temperature response of the first rolled material in the longitudinal direction on entering the rolling mill can be taken into account. This can help to ensure compliance with assured properties of the first rolled material produced, over its entire length.

The data of the further production dataset $F_f$ comprise exclusively modeled data and properties of the first rolled material or of rolled material sections of the first rolled material that are only poorly or not at all accessible to measuring means. These include, for example, temperatures of the rolled material in question or of rolled material sections on different rolling mill sections during the production process. Alternatively or in addition, the further production dataset $F_f$ can comprise one or more cooling rates of the rolled material or of rolled material sections during the production process.

Similarly, the metallurgical properties of the metallurgical dataset $K_f$ also cannot be directly recorded by measuring means during the production process, but can only be modeled. These include e.g. phase fractions $p_k$ whose evolution over time can be ascertained for example on the basis of the aforementioned system of equations (4).

Furthermore, the physical production model can be used to model such production data $P_f$, $P_i$ as, although in principle specified or recorded by measuring means, are not available due to an error (e.g. unreliably recordable temperature value due to a cooling water film on a rolled material)—in this case the missing value in a production dataset can be replaced by modeling on the basis of the physical production model.

The statistical data model can be used to ascertain from the production dataset $P_f$ of the first rolled material a second mechanical dataset $S_f$ that comprises the mechanical properties of the first rolled material after production thereof in the rolling mill. This is the same group of mechanical properties as those ascertained on the basis of the physical production model.

The statistical data model of the method according to the invention is a trained and validated statistical data model in the previously defined sense that is able to ascertain the mechanical properties of the first rolled material after production thereof in the rolling mill in the form of a second mechanical dataset $S_f$ on the basis of learned correlations. The expression 'after production' is again intended to be understood in the previously defined sense. The second mechanical dataset $S_f$ comprises the same number and the same type of mechanical properties as the first mechanical dataset $C_f$. The data of the first and second mechanical datasets $S_f$, $C_f$ therefore correspond to each other and differ only in the way they are each ascertained.

The mentioned correlations of the statistical data model are taught thereto before its use in the method according to the invention on the basis of available production datasets $P_i$ of the further rolled materials and the associated measured (i.e. ascertained in a sampling) mechanical properties $B_i$. In other words, some of the production datasets $P_i$ of the further rolled materials form the training datasets of the statistical data model used in the method according to the invention.

A first step S1 of the method according to the invention involves ascertaining the first mechanical dataset $C_f$, the further production dataset $F_f$ and the metallurgical dataset $K_f$ of the first rolled material from the production dataset $P_f$ of the first rolled material by means of the physical production model. The ascertained values of the mechanical dataset $C_f$, the further production dataset $F_f$ and the metallurgical dataset $K_f$ depend firstly on the equations or systems of equations chosen for modeling the production process and secondly on the metallurgical model parameters $\gamma$.

A second step S2 of the method according to the invention involves ascertaining the second mechanical dataset $S_f$ of the first rolled material from the production dataset $P_f$, the further production dataset $F_f$ and the metallurgical dataset $K_f$ of the first rolled material by means of the trained and validated statistical data model.

The production dataset $P_f$, the further production dataset $F_f$ and the metallurgical dataset $K_f$ form the input variables of the statistical data model, whereas the second mechanical dataset $S_f$ represents the output variables. Since the further production dataset $F_f$ and the metallurgical dataset $K_f$ each contain data that cannot be recorded by measuring means, they, together with the production dataset $P_f$, form an extended database for the statistical data model that allows a more accurate prediction of the mechanical properties by the statistical data model than would be possible if only the production dataset $P_f$ were used as input variables of the statistical data model.

A third step S3 of the method according to the invention involves determining for the production dataset $P_f$ of the first rolled material an averaged normalized distance value $d_{f,m}$ in relation to a number n of production datasets $P_i$ of the further rolled materials.

A fourth step S4 of the method according to the invention involves using the averaged normalized distance value $d_{f,m}$ to ascertain the mechanical properties $J_f$ of the first rolled material as a weighted average from the first and second mechanical datasets $C_f$, $S_f$ of the first rolled material. The weighting advantageously takes into account the position of the data of the production dataset $P_f$ of the first rolled material in relation to the data of the production datasets $P_i$ of the further rolled materials.

If the data of the production dataset $P_f$ of the first rolled material are on average 'close to' the data of the production datasets $P_i$ of the further rolled materials, this is equivalent to the first rolled material having a similar composition and/or having undergone a similar production process to the further rolled products taken into account for computing the averaged normalized distance value $d_{f,m}$. As a result, the averaged normalized distance value $d_{f,m}$ assumes a smaller numerical value compared with the case where the composition of the first rolled material is more dissimilar or the first rolled material has undergone a more greatly deviating production process than the further rolled products. In summary, the properties of and production process for the first rolled material are more similar to the further rolled products in the first case than in the second case. For this reason, the prediction accuracy of the statistical data model is higher in the first case (smaller value of $d_{f,m}$) than in the second case (larger value of $d_{f,m}$).

This circumstance is taken into account by the fact that in the fourth step S4 of the method according to the invention the mechanical properties $S_f$ predicted by the statistical data model are weighted more highly than the mechanical properties $C_f$ predicted by the physical production model. If the first rolled material is more dissimilar to the further rolled materials, the weighting accordingly shifts in the direction of the values $C_f$ predicted by the physical production model. The quotients of the mutually corresponding values of the second and first mechanical datasets $S_f$ and $C_f$ are thus weighted in proportion to the averaged normalized distance value $d_{f,m}$ of the first rolled material. Mathematically, this relationship can be expressed as $(S_{f,j}/C_{f,j}) \propto d_{f,m}$, where the index j denotes the same mechanical property in each of the first and second datasets (e.g. tensile strength $Y_s$) $S_f$ and $C_f$.

For example, the ascertainment of a single mechanical property $J_{f,j}$ of the first rolled material can be expressed using a weighting function $w(d_{f,m})$ according to $$J_{f,j} = w(d_{f,m}) \cdot S_{f,j} + (1 - w(d_{f,m})) \cdot C_{f,j} \qquad (10)$$

where the index j denotes the mechanical property in question in the group of mechanical properties $J_f$. The weighting function $w_j(d_{f,m})$ is dependent on the averaged normalized distance value $d_{f,m}$ and can be parameterized separately for each individual mechanical property with the index j, for example in the form $$w_j(d_{f,m}) = 1 - \frac{1}{1 + e^{\lambda_j(\delta_j - d_{f,m})}} \qquad (11)$$

In this case, the parameter $\delta_j$ is the function argument for which the weighting function $w_j(d_{f,m})$ assumes the value 0.5. The parameter $\lambda_j$ affects the slope of the function. The parameters $\delta_j$ and $\lambda_j$ must be selected on the basis of the predictions of the statistical data model based on the test data in such a way that, if respective predefined fault tolerances with respect to the respective mechanical properties $j_f$ are exceeded, the weighting function $w_j(d_{f,m})$ is parameterized accordingly: for example, the weighting function $w_j(d_{f,m})$ should assume a value of 0.5 for tensile strength $Y_s$ when the half fault tolerance is assumed to be 15 MPa and a value of 0.1 when the full fault tolerance is assumed to be 30 MPa, from which the corresponding values for $\delta_j$ and $\lambda_j$ follow.

According to a preferred embodiment of the method according to the invention, the mechanical properties $J_f$ of the first rolled material comprise a tensile strength $Y_s$ and/or a yield strength $T_s$ and/or an elongation at break $A_1$. These mechanical properties $J_f$ can easily also be ascertained during a physical sampling of the first rolled material, which advantageously allows a direct comparison with the values predicted by the hybrid model.

In a preferred embodiment of the method according to the invention, the averaged normalized distance value $d_{f,m}$ is formed—for example as an arithmetic mean—from n normalized distance values $d_{f,i}$ of the production dataset $P_f$ of the first rolled material in relation to a respective production dataset $P_i$ of one of the further rolled materials.

For example, a normalized distance value $d_{f,i}$ of the production dataset $P_f$ in relation to the production dataset $P_i$ can be ascertained according to $$d_{f,i} = \frac{1}{M}\sum_{k=1}^{m}|z_{k,f} - z_{k,i}| \tag{12}$$

where $z_{k,f}$ and $z_{k,i}$ are each a standardized value with the index k from the production dataset $P_f$ or from the production dataset $P_i$ (for example, a foreign element fraction, a speed or a temperature of the rolled material in question during production thereof) and where M is the number of items of data taken into account in a production dataset. In formula (12), the index f denotes variables belonging to the first rolled material, the index k denotes a component in the production dataset $P_f$ or $P_i$, while the index i identifies variables belonging to the further rolled materials. Furthermore, the standardized value $z_{k,f}$ in formula (12) can be computed according to $$z_{k,f} = \frac{x_{k,f} - x_{k,min}}{x_{k,max} - x_{k,min}} \tag{13a}$$

where $x_{k,min}$ or $x_{k,max}$ denotes the smallest or largest value of the component with the index k in the totality of all production datasets $P_i$ of the further rolled materials. In other words, the component $x_{k,f}$ with the index k in the production dataset $P_f$ of the first rolled material is related to the range of values that is defined by the smallest and largest value of the same component (index k) from the totality of the further rolled materials. For the standardized property $z_{k,i}$ in formula (12), a formula similar to formula (13a) applies:

$$z_{k,i} = \frac{x_{k,i} - x_{k,min}}{x_{k,max} - x_{k,min}} \tag{13b}$$

In formula (13b), $x_{k,i}$ denotes a component with index k in the production dataset $P_i$ of a further rolled material and $z_{k,i}$ denotes a corresponding standardized value in the production dataset of the further rolled material.

The normalized distance value $d_{f,i}$ thus represents a dimensionless measurement between the production dataset $P_f$ of the first rolled material and a production dataset $P_i$ of one of the further rolled materials. In this context, 'normalized' is intended to be understood to mean that the distance value can be ascertained regardless of the specific number and physical unit of the respective data in the individual production datasets. 'Dimensionless' is intended to be understood to mean that the variable concerned is not subject to any physical unit of measurement. In contrast to a dimensionless variable, the individual data of production datasets are usually provided with physical units; for example, a roll gap has the physical unit of a length, a cooling rate is measured in the physical units temperature per unit time, a coolant rate is measured in volumes per time, etc. Furthermore, the term 'measurement' refers to a mathematical computation rule that maps a majority of real variables to the set of positive real numbers.

A number n of smallest normalized distance values $d_{f,i}$ of the production dataset $P_f$ of the first rolled material in relation to a respective production dataset $P_i$ of one of the further rolled materials is used to calculate, on the basis of the arithmetic mean value $$d_{f,m} = \frac{1}{n}\sum_{i=1}^{n}d_{f,i} \tag{14}$$

the averaged normalized distance value $d_{f,m}$. According to the preferred embodiment of the method according to the invention, the number n of production datasets $P_i$ of the further rolled materials taken into account comprises 0.1 to 0.5 percent of the training datasets of the trained statistical data model.

In practice, the volume of training datasets used to train the statistical data model comprises several thousand rolled materials produced by the rolling mill within a continuous period, which corresponds, for example, to a production period of 1 to 2 years. It follows that about 50-100 production datasets from the volume of training datasets with which the statistical data model has been trained are used for ascertaining the averaged normalized distance value $d_{f,m}$.

The first rolled material and the further rolled materials can be divided into one or more rolled material sections by data processing means. A rolled material section preferably has a length of a few meters, for example from two to five meters. It is also possible to divide the rolled material into longer or shorter rolled material sections. The division is usually carried out in the longitudinal direction of the rolled material, which is consistent with the production direction in the rolling mill during production thereof. In the simplest case, a rolled material is divided into only a single rolled material section. The data of a respective production dataset can accordingly be recorded per rolled material section and assigned to the applicable rolled material section by data processing means. Similarly, the data of a further production dataset and of a metallurgical dataset can also be modeled per rolled material section and assigned to the applicable rolled material section by data processing means.

If the data of the production dataset of a rolled material, of the associated further production dataset and of the associated metallurgical dataset for one or more rolled material sections are available, it is also possible to ascertain the mechanical properties, ascertained therefrom, of the relevant rolled material according to the one or more rolled material sections. According to a further preferred embodiment of the method according to the invention, the mechanical properties $J_f$ of the first rolled material are therefore ascertained for at least one rolled material section of the first rolled material. This allows an even more precise modeling of the production process to be achieved and the mechanical properties $J_f$ of the first rolled material to be ascertained on the basis of the position of a rolled material section within the rolled material.

The rolling mill has a specific number of roll stands, wherein, viewed in the production direction, a first roll stand is encountered by a rolled material first and a last roll stand is encountered last. Furthermore, the rolling mill generally has a specific number of cooling devices, a specific number of rolling mill sections and at least one coiling device. For example, a rolling mill section may extend between one of the roll stands of the rolling mill and the—viewed in the production direction—directly downstream roll stand, or from the last roll stand to a coiling device of the rolling mill.

In a preferred embodiment of the method according to the invention, in which the rolling mill has N roll stands $R_1, \ldots, R_N$, L cooling devices $Q_1, \ldots, Q_L$, Z rolling mill sections $A_1, \ldots, A_Z$ and at least one coiling device, the production datasets of the first rolled material and the further rolled materials $P_f$, $P_i$ each comprise at least one of the following manipulated or measured variables for at least one rolled material section of the first rolled material and the further rolled materials:

- one or more foreign element fractions, such as percent by weight of carbon, silicon, manganese, copper, nickel, titanium, chromium, sulfur, phosphorus, calcium, etc., in the respective rolled material section,
- a thickness and/or a width of the rolled material section before entering a first roll stand $R_1$ of the rolling mill,
- a thickness and/or a width of the rolled material section after exiting a last roll stand $R_N$ of the rolling mill,
- at least one temperature of the respective rolled material section recorded by measuring means, preferably a temperature of the respective rolled material section recorded immediately before entering the rolling mill and/or a temperature of the respective rolled material section recorded in one of the rolling mill sections $A_1, \ldots, A_Z$ (e.g. using a pyrometric measurement) and/or a temperature of the respective rolled material section recorded during the coiling of the first rolled material or the further rolled materials,
- at least one roll gap value of one of the roll stands $R_1, \ldots, R_N$ when the rolled material section passes through the respective roll stand $R_1, \ldots, R_N$ of the rolling mill,
- at least one coolant stream emitted by one of the cooling devices $Q_1, \ldots, Q_L$ of the rolling mill when the rolled material section passes through the operating range of the respective cooling device $Q_1, \ldots, Q_L$, or
- at least one speed of the rolled material section in one of the rolling mill sections $A_1, \ldots, A_Z$ of the rolling mill.

By taking into account individual specialisms of the rolling mill or individual influencing factors for modeling the production process, even more precise ascertainment of the mechanical properties $J_f$ of the first rolled material can be achieved.

The mentioned manipulated or measured variables are each recorded by data processing means during the production of a rolled material section of the first rolled material or the further rolled materials in the rolling mill and are assigned to the corresponding rolled material section by data processing means. The mentioned manipulated or measured variables are generally easily and permanently recordable by measuring means or data processing means, even under harsh production conditions, and, for the statistical data model, are therefore reliably available input data for which data errors can be expected only very rarely.

The roll gap value of a roll stand is understood to mean the distance between two working rollers of a roll stand in the thickness direction of the rolled material when it passes through the roll stand in question. The operating range of a cooling device is understood to mean the area within the rolling mill in which the cooling device in question brings about a cooling effect for the rolled material passing through the rolling mill or for the rolled material section. For example, the operating range of a cooling device may coincide with its spray range. In addition, the rolled material may have a different speed in each of the individual rolling mill sections $A_1, \ldots, A_Z$ during production due to the thickness reduction carried out by the respective roll stands. The speeds in the individual rolling mill sections can either be recorded by measuring means directly (e.g. using contactless speed measurement methods) or ascertained, for example, from a rotation speed and a diameter of the working rollers of a roll stand and the thickness reduction for the rolled material on the roll stand in question.

According to a further preferred embodiment of the method according to the invention, the further production dataset $F_f$ for at least one rolled material section of the first rolled material comprises at least one modeled cooling rate $q_z$ and/or at least one modeled temperature value $T_z$ of the rolled material section when passing through at least one of the rolling mill sections $A_1, \ldots, A_Z$ of the rolling mill.

In a further preferred embodiment of the method according to the invention, the metallurgical properties of the metallurgical dataset $K_f$ of the first rolled material comprise phase fractions $p_h$ and/or morphological characteristics $a_k$ (such as a lamella spacing in the perlite, a ferrite or austenite grain size, a plate thickness in the bainite, a package size of the martensite, an averaged displacement density or a degree of recrystallization) of different metallurgical phases of the first rolled material or of at least one rolled material section of the first rolled material. For example, the metallurgical phase fractions $p_k$ are expressed in percent by weight.

For example, the evolution of a morphological characteristic ah of a rolled material during the production process in a rolling mill can be described by an equation in the form $$\frac{da_h}{dt} = f_1(T1, \{a_h\}) + f_2(T2, \{a_h\}, \dot{\varphi}) \tag{15}$$

the index h representing a specific phase, for example austenite, ferrite or perlite. In equation (15), $f_1$ denotes a mathematical function that describes the evolution of the morphological characteristic ah over time on the basis of the prevailing morphological characteristics (represented by the symbol $\{a_h\}$) and the temperature T1 outside a roll gap. In contrast, $f_2$ denotes a function that describes the microstructure evolution as a result of reshaping in a roll gap on the basis of the given morphology $\{a_h\}$, the time derivative of the degree of reshaping $\partial_t \varphi$ of the rolled material in the roll gap and a temperature T2 in the roll gap.

After production in the rolling mill, especially after production in a hot rolling mill, the rolled material produced usually has an increased temperature of up to 800° C.

Subsequently, the rolled material is usually stored or actively cooled until it has reached an ambient temperature. Only after this temperature equalization is complete is sampling generally performed, which can be used to compare the mechanical properties ascertained by a model with the measured mechanical properties of a physical sample. During the cooling phase to ambient temperature, carbide and nitride precipitations take place in the material of the rolled material, which influence the mechanical properties even after the production process in the rolling mill is complete. In particular, carbide and nitride precipitations with a size of up to 10 nm cause the material to harden.

Therefore, in order to be able to better compare the mechanical properties ascertained by sampling with the mechanical properties $J_f$ of a first rolled material that are predicted by a model, in a further preferred embodiment of the method according to the invention a fifth step S5 involves subjecting the ascertained mechanical properties $J_f$ of the first rolled material to a cooling correction in which carbide and nitride precipitations in the first rolled material are taken into account during cooling after production in the rolling mill.

The precipitation processes are time- and temperature-dependent. In particular if the rolled material produced passes through the cooling phase in the form of a strip wound into a coil, the precipitation volumes and the associated precipitation hardening over the strip length differ due to the different cooling conditions for different strip positions in the coil. Particularly preferably, a cooling correction is applied to individual rolled material sections of a rolled material, since the rolled material sections correspond to a respective strip position of the material in a coil. This allows the different cooling behavior of individual rolled material sections to be mapped particularly accurately.

The cooling correction is carried out, for example, by means of tabulated correction functions, which are ascertained in advance, i.e. independently of the actual production process for a rolled material, on the basis of a further metallurgical model. Each of the mechanical properties $J_f$ is corrected with its own correction function. For example, the function value of a correction function is a multiplication factor that must be applied to each of the uncorrected mechanical properties $J_f$.

The arguments of the correction functions (i.e. their input variables) are, for example, specific alloy constituents (in particular niobium, titanium and vanadium) of a rolled material, a coiling temperature of the rolled material or of a rolled material section, and the inner and outer radius of the coil in question. In this context, 'tabulated' means that the correction functions are ascertained only for a certain number of values (e.g. for 10-50 values) of an argument. For input variables between these values, the corrections for each of the mechanical properties $J_f$ of the first rolled material are ascertained by appropriate interpolation of the function values.

The range of the coiling temperature for which the correction functions are ascertained is preferably in a range from 600° C. to 750° C., the precipitation kinetics relevant to the correction functions being negligible below 600° C., and 750° C. corresponding to a maximum coiling temperature in practice. In addition, the correction functions are ascertained on the basis of a complete phase conversion of the rolled material before the coiling, i.e. the effects of a perlite or cementite formation in the rolled material are ignored.

In the method according to the invention for creating a hybrid model, the hybrid model essentially corresponds to the hybrid model from the aforementioned method according to the invention for determining mechanical properties $J_f$ of a first rolled material.

In the method according to the invention for creating a hybrid model for determining mechanical properties $J_f$ of a first rolled material produced in a rolling mill, in particular in a hot rolling mill, the hybrid model accordingly comprises production datasets $P_i$ of further rolled materials produced in the rolling mill, a physical production model and a statistical data model.

The production datasets $P_i$ of the further rolled materials are understood in the previously defined sense, wherein the further rolled materials in turn form a first set $I_1$. Furthermore, for each of the production datasets $P_i$ of the further rolled materials there is a corresponding sampling dataset $B_i$ of the rolled material in question available that comprises the respective mechanical properties of the further rolled material ascertained by means of a sampling device after production of the further rolled material in the rolling mill.

The physical production model has a set of metallurgical model parameters $\gamma$ in the sense defined above for modeling the production process for the further rolled materials, and so each of the production datasets $P_i$ can thus be used to ascertain a first mechanical dataset $C_i$, comprising the respective mechanical properties after production in the rolling mill, a further production dataset $F_i$, comprising further production data during production in the rolling mill, and a metallurgical dataset Ki, comprising metallurgical properties during production in the rolling mill, for each of the further rolled materials. The terms 'during production' and 'after production' are again intended to be understood in the previously described sense.

Furthermore, the method according to the invention for creating a hybrid model comprises a statistical data model that can be used to ascertain a second mechanical dataset $S_i$ for each of the further rolled materials from the respective production dataset $P_i$ of the further rolled material, which mechanical dataset comprises the mechanical properties of the further rolled material after production thereof in the rolling mill. At the beginning of the method according to the invention, the statistical data model is an as yet untrained and unvalidated statistical data model in the previously defined sense.

One or more consecutive iterations of a first step S1' of the method according to the invention for creating a hybrid model involve using the physical production model to ascertain, i.e. in the aforementioned sense to model, for each of the production datasets $P_i$ of the further rolled materials the respective corresponding first mechanical dataset and further production and metallurgical datasets $C_i$, $F_i$, Ki. The term 'iteration' is intended to be understood algorithmically as the performance of the same recurring computation processes—in the specific case the ascertainment of the mentioned datasets.

Again—as explained above in regard to the method according to the invention for determining mechanical properties $J_f$ of a first rolled material—the data of the respective first mechanical dataset $C_i$, the respective further dataset $F_i$ and the respective metallurgical dataset $K_i$ are, in mathematical respects, explicitly dependent on the metallurgical model parameters $\gamma$, this dependency being able to be expressed by the notation $C_i(\gamma)$, $F_i(\gamma)$ and $K_i(\gamma)$, respectively.

Each iteration is followed by a first measurement function si being used for component-by-component ascertainment, for the totality of the first mechanical datasets $C_i$ of the further rolled materials ascertained in the most recently performed iteration, of a (in the previously defined sense mathematical) measure of the deviation from the corresponding sampling datasets $B_i$ of the further rolled materials. In this context, 'component-by-component' means that the measure of the deviation for each individual mechanical property in the first mechanical datasets $C_i$ or in the sampling datasets $B_i$ is ascertained separately. The first measurement function $\varepsilon_1$ may be embodied as a square shape, for example as $$\varepsilon_1 = \frac{\sqrt{\sum_i (C_{i,j}(\gamma) - B_{i,j})^2 \cdot w_i}}{\sqrt{\sum_i (C_{i,j}(\gamma))^2 \cdot w_i}} \quad (16)$$

or $$\varepsilon_1 = \frac{\sqrt{\sum_i (C_{i,j}(\gamma) - B_{i,j})^2 \cdot w_i}}{\sqrt{\sum_i (C_{i,j}(\gamma) + B_{i,j})^2 \cdot w_i}} \quad (17)$$

where the index i denotes a specific rolled material of the further rolled materials and the expression $w_i$ is an individual weighting factor for the first mechanical dataset C and the sampling dataset $B_i$ of the further rolled material with index i. In the simplest case, all weighting factors $w_i$ can be set to 1.

If the value of the first measurement function si for at least a single mechanical property (identified by the index j in each of formulae (16) and (17)) in the first mechanical datasets $C_i$ of the further rolled materials is greater than a specified limit $\varepsilon_{max}$, the metallurgical model parameters $\gamma$ are varied and, in a further iteration, the first mechanical datasets, the further production datasets and the metallurgical datasets $C_i$, $F_i$, $K_i$ of the further rolled materials are re-ascertained on the basis of the physical production model with the modified metallurgical model parameters $\gamma$. For example, the specified limit $\varepsilon_{max}$ can be two to three times the measurement accuracy of one of the mechanical properties $B_{i,j}$ ascertained during a sampling process. For example, the specified limit $\varepsilon_{max}$ can be two to three megapascals.

In this context, the expression 'varied' means that the numerical values of the metallurgical model parameters $\gamma$ are modified. The purpose of this variation is to model the production process for the further rolled materials more accurately in the following iteration and to minimize the value of the first measurement function si used as a measure of the accuracy of the modeling. A corresponding minimization of the value of the first measurement function $\varepsilon_1$ corresponds to a so-called 'least squares fit' method and can be achieved, for example, by a gradient method according to Levenberg-Marquart (corresponding to http://people.duke.edu/~hpgavin/ce281/lm.pdf).

If the value of the first measurement function $c_i$ for all mechanical properties in the first mechanical datasets $C_i$ of the further rolled materials is less than or equal to the limit $\varepsilon_{max}$, there is a sufficiently accurate simulation of the production process for the totality of the further rolled materials. Therefore, the production datasets $P_i$ of the further rolled materials together with the further production and metallurgical datasets $F_i$ and $K_i$ of the further rolled materials ascertained in the most recently performed iteration are transferred to the statistical data model as input variables and the corresponding sampling datasets $B_i$ are transferred to the statistical data model as target variables. The terms 'input variables' and 'target variables' are again intended to be understood in the aforementioned sense in relation to statistical data models. The number of different target variables transferred to the statistical data model corresponds to the number of mechanical properties present in each sampling dataset: for example, three target variables are transferred to the statistical data model if the sampling datasets $B_i$ each comprise a tensile strength $Y_s$, a yield strength $T_s$ and an elongation at break $A_1$.

Accordingly, the statistical data model comprises a separate statistical partial data model for each target variable, which partial data model exists independently of the other partial data models and, after appropriate training, is able to predict the respective corresponding mechanical variable. However, the input variables for training the partial data models are the same for all partial data models.

A second step S2' involves training the statistical data model on the basis of the transferred input and target variables using a first machine learning method $V_1$. Each partial data model can be trained on the basis of the same first machine learning method $V_1$; the machine learning methods can alternatively also be different for each partial data model. In this context, the designation 'first' machine learning method is intended to be understood as the learning method used for the purpose of training the data model or a partial data model.

Various machine learning methods, such as methods based on decision trees such as random forest or gradient boosting trees, so-called support vector machines, artificial neural networks, evolutionary algorithms or combinations of multiple data models (ensemble learning), are known from the specialist literature. As an example, Friedman et al., The Elements of Statistical Learning, Springer series in statistics, 2001, ISBN 0-387-95284-5, is cited as disclosure for the process of machine learning.

A third step S3' involves validating the trained statistical data model on the basis of production datasets $P_i$ and sampling datasets $B_i$ of rolled materials from a second set $I_2$, which is disjunct from the first set $I_1$. For this purpose, the further production datasets $F_i$ and metallurgical datasets $K_i$ are ascertained for the rolled materials of the second set $I_2$ by means of the physical production model, said datasets, together with the production datasets $P_i$ of the rolled materials of the second set $I_2$, being supplied to the trained statistical data model as input variables. From these, the trained statistical data model ascertains corresponding second mechanical datasets $S_i$ for the rolled materials of the second set $I_2$. For these second mechanical datasets $S_i$, a second measurement function $\varepsilon_2$ is used for component-by-component ascertainment of a measure of a deviation from the corresponding sampling datasets $B_i$. The expression 'component-by-component' is intended to be understood in the previously described meaning, i.e. the second measurement function $\varepsilon_2$ is used to ascertain for each individual mechanical property in the second mechanical datasets $S_i$ a deviation from the respective corresponding mechanical property in the corresponding sampling datasets $B_i$.

For example, the mean absolute error MAE for the second measurement function $\varepsilon_2$ is used according to $$\varepsilon_2 = MAE = \frac{1}{n} \sum_i |S_{i,j} - B_{i,j}| \quad (18)$$

where the index i denotes the datasets of the rolled materials from the second set $I_2$ and the index j denotes a single mechanical property (e.g. a tensile strength $Y_s$, a yield strength $T_s$ or an elongation at break $A_1$) within the individual datasets $S_i$ and $B_i$.

The production datasets $P_i$ and sampling datasets $B_i$ of the second set $I_2$ are thus the test dataset for the statistical data model. To perform the second and third steps S2' and S3', the data basis of a rolling mill covering a total period of 2 years is divided into two volumes, for example, the division being carried out within continuous production periods: for example, the available production datasets $P_i$ as input variables and sampling datasets $B_i$, as those that form training datasets for the statistical data model, can extend over the first 1.5 years of the period, while the test dataset contains the production datasets $P_i$ and sampling datasets $B_i$ of rolled materials for the last 6 months.

The first machine learning method $V_1$, which is used as a basis for the statistical data model (or a respective partial data model), can be firmly chosen from the outset. Alternatively, it is also possible to train the statistical data model (or each partial data model) on the basis of the same training dataset by means of different machine learning methods and to verify the resulting predicted mechanical properties of the training dataset using the same test dataset, that learning method whose prediction has the least deviation from the sampling data $B_i$ of the test datasets ultimately being selected.

According to one embodiment of the method according to the invention for creating a hybrid model, the mechanical properties $J_f$ of the first rolled material and the sampling datasets $B_i$, the first mechanical datasets C and the second mechanical datasets $S_i$ of the further rolled materials each comprise a tensile strength $Y_s$ and/or a yield strength $T_s$ and/or an elongation at break $A_1$.

According to a further embodiment of the method according to the invention for creating a hybrid model, performance of the first step S1' is preceded by the respective sampling dataset $B_i$ from each of the further rolled material that corresponds to the production dataset $P_i$ being transformed to a normalized sample geometry according to Oliver's formula.

The mechanical properties of a sampling dataset $B_i$ of individual samples cannot be combined in a common training dataset for generating a statistical data model without additional information, since the samples usually have a respective variety- and thickness-dependent geometry. Due to this geometry dependence of different samples, the mechanical properties ascertained in a sampling process using a sampling device cannot be compared across all varieties of rolled materials (for example for rolled materials made of different steel grades). In order to compensate for these differences in geometry and variety, it is therefore necessary to relate the mechanical properties of a sampling dataset $B_i$ to a standard geometry.

The elongation at break $A_1$ in percent is defined as the quotient of the change in length $\Delta L$ and an initial measurement length $L_0$ of a sample piece. For example, the initial measurement length $L_0$ can be defined differently depending on the steel grade, thickness, standard or production specification. The initial measurement length can also be variable and depend on the cross-sectional area $S_0$ of the sample piece. So-called proportional samples have a ratio of $L_0 = 5.65 \cdot (S_0)^{0.5}$, for example. For a rectangular sample cross section, the cross-sectional area is calculated according to $S_0 = b_0 \cdot t_0$, where $b_0$ is the sample width and $t_0$ is the sample thickness according to ISO 6892-1:2019 Metallic Materials—Tensile testing—Part 1: Method of Test at room temperature, ASTM E8/E8M—16AE1 Standard Test Methods for Tension Testing of Metallic Materials.

In an equation disclosed in accordance with the standard ISO 2566-1, the exponential factor n is specified as having the value 0.4 for steel. However, this is not entirely true or too inaccurate for modern steel-based materials, as explained for example in Hanlon et al. (2015), Critical Assessment 10: Tensile elongation of strong automotive steels as function of testpiece geometry, Materials Science and Technology, 31:4, 385-388, DOI: 10.1179/1743284714Y.0000000707.

Furthermore, the sample orientation, i.e. the orientation in relation to a production direction, may be defined differently. The orientation can be in the longitudinal direction (longitudinal, l) or in the transverse direction (transverse, t), in each case with reference to the rolling direction or at a specific angle. Due to the rolling-dependent anisotropy of the metallurgical microstructure, the results may differ.

Therefore, in order to make all measured values for the elongation at break $A_1$ comparable, they are converted, for example using Oliver's formula $$A_{y,o} = A_{x,o} \left[ \frac{L_{0,x,o}}{\sqrt{S_{0,x,0}}} \right]^{n_{i,x \to y,o}} \left[ \frac{\sqrt{S_{0,y,o}}}{L_{0,y,o}} \right]^{n_{i,x \to y,o}} \quad (19)$$

from a sample geometry x with the orientation o, in which the ascertainment of the elongation at break of a specific sample was carried out, to a common sample geometry y with the same orientation o. For example, the orientation of the sample during sampling may be horizontal or longitudinal in relation to the rolling direction. The term 'sample geometry' refers to the original length of the sample (for example 50 mm or 80 mm). In formula (19), therefore, $A_{x,o}$ and $A_{y,o}$ denote the elongation at break with respect to a specific sample geometry and orientation o, $L_{0,x/y,o}$ denotes the original sample length x or y in the orientation o, $S_{0,x/y,o}$ denotes the original sample cross section for the sample length x or y in the orientation o and $n_{i,x \to y}$ denotes an individual exponential factor, dependent on the type (e.g. steel grade), the sample geometry and the orientation o of the respective sample, for converting from the sample geometry x in the orientation o, in which the actual sampling was carried out, to a common sample geometry y with the same orientation o.

As only values of samples with the same orientation o can be converted into each other using formula (19), the mechanical properties for the respective sample orientation must be included in the sampling data $B_i$ as separate mechanical properties (e.g. one value each for the elongation at break $A_1$ in the longitudinal and transverse directions). Alternatively, however, the respective mechanical properties can also be transferred from a sample orientation using an additive correction term to a different sample orientation (e.g. according to $A_1 = A_t + \Delta A$ with $\Delta A$ as the correction term), provided that a value for the additive correction term has been known, for example empirically ascertained.

According to a further embodiment of the method according to the invention for creating a hybrid model, the mechanical properties $J_f$ of the first rolled material and the first mechanical datasets C and the second mechanical datasets $S_i$ of the further rolled materials are each ascertained for at least one rolled material section of the first rolled material and the further rolled materials. The advantages and technical effects correspond to those of the method according to the invention for determining mechanical properties $J_f$ of a first rolled material using a hybrid model.

Analogously to the method according to the invention for determining mechanical properties $J_f$ of a first rolled material using a hybrid model, in a further embodiment of the method according to the invention for creating a hybrid model the rolling mill has N roll stands $R_1, \ldots, R_N$, L cooling devices $Q_1, \ldots, Q_L$, Z rolling mill sections $A_1, \ldots, A_Z$ and at least one coiling device. The production datasets of the first rolled material and the further rolled materials $P_f$, $P_i$ each comprise at least one of the following manipulated or measured variables for at least one rolled material section of the first rolled material and the further rolled materials:

one or more foreign element fractions in the rolled material section,
a thickness and/or a width of the rolled material section before entering a first roll stand $R_1$ of the rolling mill,
a thickness and/or a width of the rolled material section after exiting a last roll stand $R_N$ of the rolling mill,
at least one temperature of the rolled material section recorded by measuring means, preferably a temperature of the rolled material section recorded immediately before entering the rolling mill and/or a temperature of the rolled material section recorded in one of the rolling mill sections $A_1, \ldots, A_Z$ and/or a temperature of the rolled material section recorded during the coiling of the first rolled material or the further rolled materials,
at least one roll gap value of one of the roll stands $R_1, \ldots, R_N$ when the rolled material section passes through the respective roll stand $R_1, \ldots, R_N$ of the rolling mill,
at least one coolant stream emitted by one of the cooling devices $Q_1, \ldots, Q_L$ of the rolling mill when the rolled material section passes through the operating range of the respective cooling device $Q_1, \ldots, Q_L$, or
at least one speed of the rolled material section in one of the rolling mill sections $A_1, \ldots, A_Z$ of the rolling mill.

Preferably, the further production dataset $F_i$ for at least one rolled material section of each of the further rolled materials comprises at least one modeled cooling rate $q_z$ and/or at least one modeled temperature value $T_z$ of the respective rolled material section when passing through at least one of the rolling mill sections $A_1, \ldots, A_Z$ of the rolling mill. Particularly preferably, the datasets $K_i$ of the further rolled materials comprise phase fractions $p_h$ and/or morphological characteristics $a_k$ of different metallurgical phases of the further rolled materials or of at least one rolled material section of the further rolled materials.

Again, advantages and technical effects correspond to those of the method according to the invention for determining mechanical properties $J_f$ of a first rolled material using a hybrid model.

BRIEF DESCRIPTION OF THE DRAWINGS

The above-described properties, features and advantages of this invention, and the manner in which they are achieved, will become clearer and more clearly understandable in conjunction with the following description of an exemplary embodiment, which will be explained in more detail in conjunction with the figures, in which.

DETAILED DESCRIPTION

Parts that correspond to one another are provided with the same reference signs in all of the figures.

Figure 1:
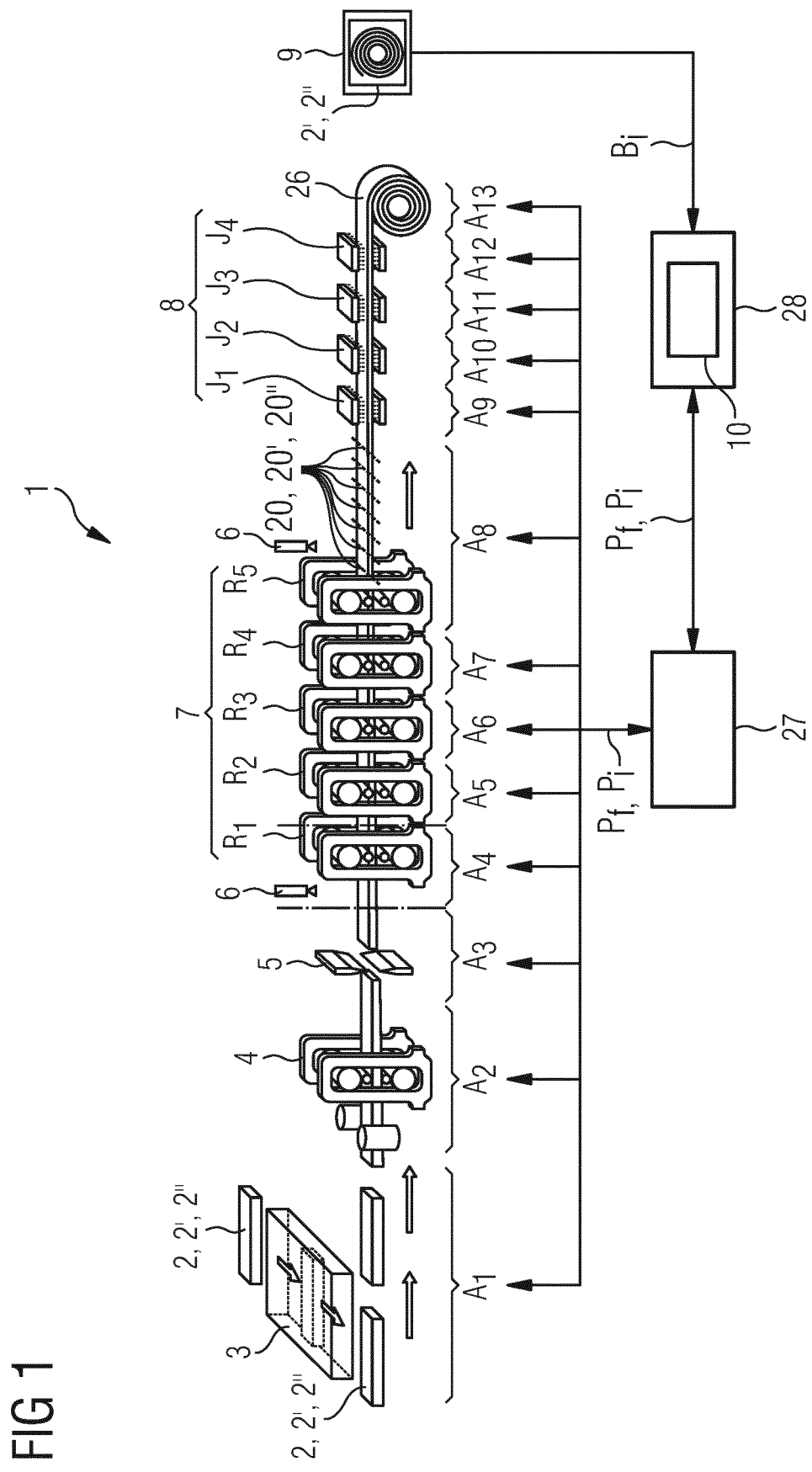
FIG. 1 (FIG. 1) schematically shows a hot rolling mill comprising a central computation unit having the hybrid model according to the invention, FIG. 2 (FIG. 2) shows a flowchart for the method according to the invention for determining mechanical properties of a first rolled material on the basis of a hybrid model according to the invention, FIG. 3 (FIG. 3) schematically shows the position of input and output data of the statistical data model, and FIG. 4 (FIG. 4) shows a flowchart of the method according to the invention for creating a hybrid model.

FIG. 1 schematically shows a hot rolling mill 1. The hot rolling mill 1 comprises a heating furnace 3, a roughing line 4, a cropping shear 5, a finishing rolling line 7, a cooling section 8 and a coiling device 26. The finishing rolling line 7 comprises five roll stands $R_1, \ldots R_5$; the cooling section 8 comprises four cooling devices $Q_1 \ldots Q_4$. A rolled material 2, 2', 2" in the form of a slab is introduced into the heating furnace 3 and, after heating, heated to an increased temperature, for example to 1100° C. to 1200° C., and then transported in the production direction of the hot rolling mill 1 (shown in FIG. 1 by a horizontal arrow pointing to the right) in the direction of the roughing line 4.

In the roughing line 4, a first thickness reduction for the rolled material 2, 2', 2" is carried out, said rolled material being rolled from a slab format to a so-called roughed strip. Arranged downstream of the roughing line 4 when viewed in the production direction is a cropping shear 5, which can be used to cut off the strip head or the strip end of the roughed strip, since these sections of the roughed strip usually have to be scrapped. After passing through the cropping shear 5, the roughed strip enters the finishing rolling line 7, in which it is rolled to a specified final thickness. Furthermore, temperature measuring devices 6 in the form of a pyrometer are" arranged immediately upstream of the first roll stand $R_1$ and immediately downstream of the last roll stand $R_5$—in relation to the production direction of the hot rolling mill 1—to contactlessly record a surface temperature of the rolled material 2, 2', 2.

After exiting the last roll stand $R_5$, the rolled material 2, 2', 2 passes through" a cooling section 8, in which it is cooled to a coiling temperature by applying coolant by way of the cooling devices $Q_1 \ldots Q_4$. After leaving the operating range of the last cooling device $Q_4$, the rolled material 2, 2', 2 is" wound into a coil by a coiling device 26.

In line with the mentioned specialisms, the hot rolling mill 1 is divided into individual rolling mill sections $A_1 \ldots A_Z$ with Z=13 by data processing means. In FIG. 1, the rolling mill section $A_4$, which comprises the area of the first roll stand $R_1$ and the infeed-side pyrometer 6, is symbolically delimited by dash-dotted lines. The production process for the rolled material 2, 2', 2" in the hot rolling mill 1 is controlled or regulated on the basis of the respective production parameters $P_f$, $P_i$ using an installation controller 27.

The installation controller 27 is connected to the specialisms of the individual rolling mill sections $A_1 \ldots A_{13}$ by data processing means, this being symbolized in FIG. 1 by the bidirectional arrows. From the point of view of the installation controller 27, the production parameters $P_f$, $P_i$ comprise both output data (e.g. default values for the roll gap of the individual roll stands $R_1 \ldots R_5$), which are sent to the respective specialisms, and input data (such as a production speed in the respective rolling mill section or measured temperature values), which the installation controller 27 receives from the individual specialisms.

The rolled material 2, 2', 2" is divided into a, preferably multiple, rolled material section(s) 20, 20', 20" of, for example, two to 5 meters in length by data processing means. The rolled material sections 20, 20', 20" are tracked during production in the rolling mill 1: this makes it possible to assign short-term fluctuations in the applicable process parameters $P_f$, $P_i$ to individual rolled material sections 20, 20', 20" and to record said fluctuations over the length of the rolled material 2, 2', 2".

After the production process has concluded, material samples are taken from some of the rolled materials 2', 2" produced in the hot rolling mill 1 by means of a sampling device 9, the mechanical properties $B_i$ of which material samples are measured in a test laboratory, for example, and are transferred as sampling data $B_i$ together with the corresponding production data $P_i$ from the installation controller 27 to a central computation unit 28, which is embodied as a computer or programmable logic controller (PLC) and comprises the hybrid model 10 according to the invention. Production data $P_f$ of rolled materials 2 that are not sampled, i.e. for which no sampling data are ascertained, are also transferred from the installation controller 27 to the central computation unit 28, this being symbolized by a bidirectional arrow between the installation controller 27 and the central computation unit 28. In FIG. 1, the hybrid model 10 according to the invention is represented by means of a rectangular symbol within the central computation unit 28. The sampling device 9 and the central computation unit 28 are not part of the hot rolling mill 1.

Figure 2:
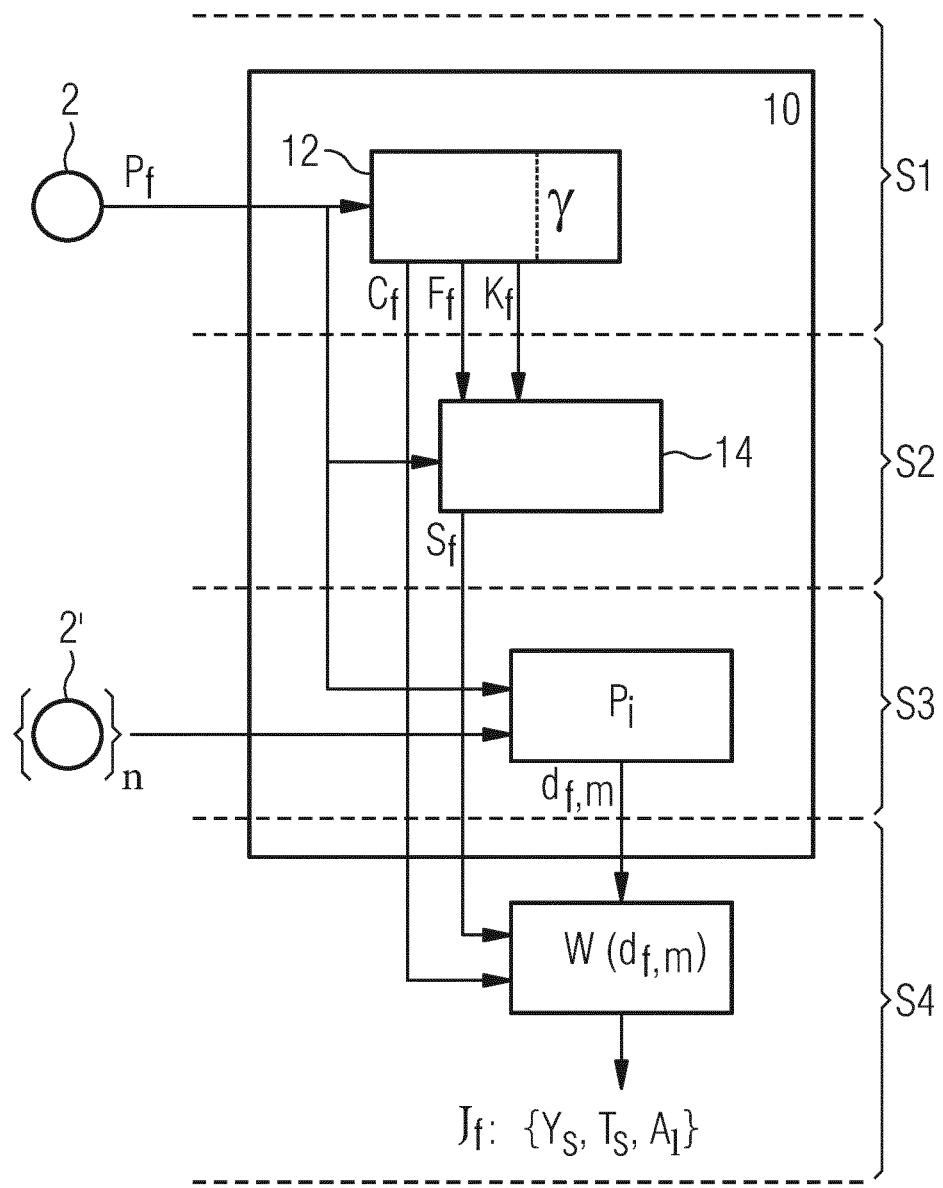
Figure 3:
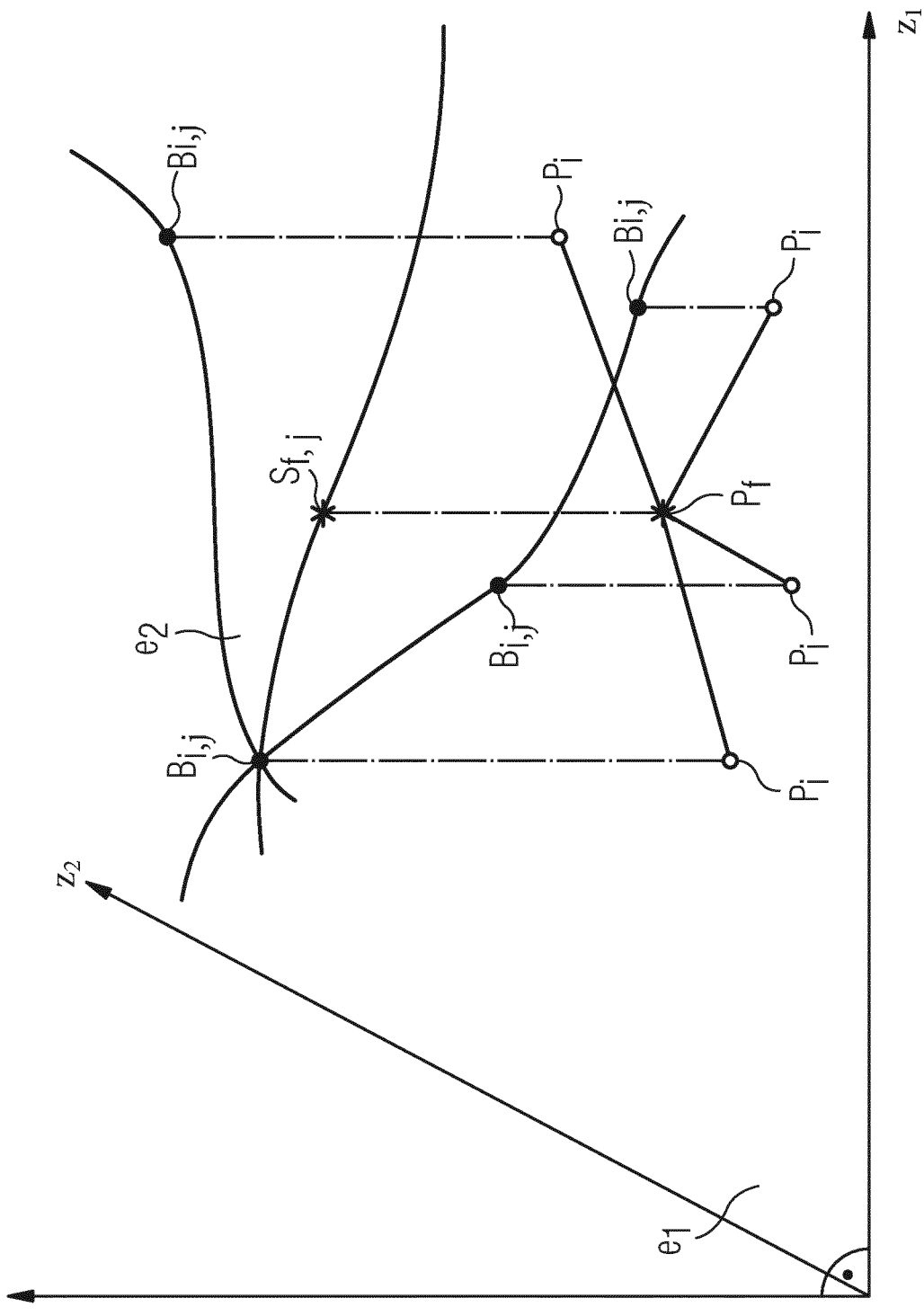

FIG. 2 (FIG. 2) shows a data flow diagram for the method according to the invention for determining mechanical properties $J_f$ of a first rolled material 2 produced in a hot rolling mill 1 with process steps $S_i$, S2, S3 and S4 on the basis of a hybrid model 10 according to the invention. The hybrid model 10 comprises production datasets $P_i$ of further rolled materials 2' produced in the rolling mill 1, a physical production model 12 and a trained and validated statistical data model 14 as structural components and is shown in FIG. 2 using a broad line thickness. These structural components of the hybrid model 10 are each shown in FIG. 2 as rectangular symbols. Data of the first rolled material or the further rolled materials 2, 2' are identified by a circle symbol or a circle symbol with set braces. The sequentially performed steps $S_i$ to S4 are shown in FIG. 3 by horizontal dashed lines. Arrows symbolize a data flow in which the data belonging to or coming from a source object are transmitted in the direction of the arrow to a target object.

Furthermore, the production datasets $P_i$, the physical production model 12 and the data model 14 themselves can comprise data structures (for example a chronological sequence of individual data in the production datasets $P_i$), internal computation rules (for example a heat conduction equation or the empirical metallurgical equations of the physical production model 12), and also relations between different data (for example links between data within the trained and validated statistical data model 14 when ascertaining a first mechanical dataset $C_f$ from the input variables of the data model 14). The production datasets $P_i$, the physical production model 12 and the data model 14 can also each comprise further internal parameters: these include, for example, the metallurgical model parameters γ or internal parameters of the statistical data model 14, which govern the reaction thereof to input variables. The mentioned data structures, internal computation rules, relations between data and internal parameters are each realized in the present exemplary embodiment as data or programming structures in the central computation unit 28, meaning that the method according to the invention for determining mechanical properties $J_f$ of a first rolled material 2 can be carried out as a program by the central computation unit 28.

The first step S1 of the method according to the invention involves transferring a production dataset $P_f$ of a first rolled material 2 to the physical production model 12 as an input variable. The physical production model 12 and the metallurgical model parameters γ are used to ascertain a first mechanical dataset $C_f$, a further production dataset $F_f$ and a metallurgical dataset $K_f$ for the first rolled material 2 from said input variable. For this purpose, the central computation unit 28 solves physical equations (for example comprising a thermal conduction equation and equations for the formation of metallurgical phases according to the aforementioned equations (1) to (4)) with applicable boundary conditions (for example according to equation (5)). According to the present exemplary embodiment, the further production dataset $F_f$ comprises temperatures and cooling rates of the first rolled material 2 during production thereof in the hot rolling mill 1, while the metallurgical dataset $K_f$ comprises phase fractions $p_k$ and/or morphological characteristics $a_k$ of the first rolled material 2 during production thereof in the hot rolling mill 1.

Furthermore, the central computation unit 28 ascertains the mechanical properties of the first rolled material 2 in the form of the first mechanical dataset $C_f$ from the production dataset $P_f$ of the first rolled material 2, from the metallurgical model parameters γ and by means of empirical metallurgical equations (for example according to the aforementioned equations (6) to (9)). According to the exemplary embodiment, the first mechanical dataset $C_f$ comprises a tensile strength $Y_s$, a yield strength $T_s$ and an elongation at break $A_1$ and is stored for the fourth step S4 of the method according to the invention, while the further production dataset $F_f$ and the metallurgical dataset $K_f$ are supplied to the statistical data model 14 as additional input variables.

The second step S2 involves ascertaining the second mechanical dataset $S_f$ of the first rolled material 2 from the production dataset $P_f$, the further production dataset $F_f$ and the metallurgical dataset $K_f$ of the first rolled material 2 using the trained and validated statistical data model 14 and storing it for the fourth step S4 of the method according to the invention. In this case, according to the exemplary embodiment, the second mechanical dataset $S_f$ again comprises a tensile strength $Y_s$, a yield strength $T_s$ and an elongation at break $A_1$ of the first rolled material 2.

The third step S3 involves determining for the production dataset $P_f$ of the first rolled material 2 an averaged normalized distance value $d_{f,m}$ in relation to n production datasets $P_i$ (symbolized in FIG. 2 by set braces with index n) of the further rolled materials 2', this being shown schematically in FIG. 3.

The fourth step S4 involves using the averaged normalized distance value $d_{f,m}$ to ascertain the mechanical properties $J_f$ of the first rolled material 2 as a weighted average from the first and second mechanical datasets $C_f$, $S_f$ of the first rolled material 2. The weighting is performed on a component-by-component basis, i.e. separately for each mechanical property of the first and second mechanical datasets $C_f$ and $S_f$, the quotient $C_{f,j}/S_{f,j}$ of the respective mechanical property of the second and first mechanical datasets $S_f$, $C_f$ being weighted in proportion to the averaged normalized distance value $d_{f,m}$. This means that the lower the value of $d_{f,m}$, the stronger the weight of the relevant mechanical property from the second mechanical dataset $S_f$ in relation to that from the first mechanical dataset $C_f$. Weighting is carried out on the basis of the aforementioned formula (10), a suitable weighting function $w(d_{f,m})$ such as that of formula (11) being used.

FIG. 3 uses a simplified statistical data model 14, the input variables (corresponding to the production datasets $P_f$ and $P_i$, the further production datasets $F_f$ and $F_i$ and the metallurgical datasets $K_f$ and $K_i$ of the first rolled material and the further rolled materials 2 and 2') of which comprise only two standardized production parameters $z_1$ and $z_2$ in total, to schematically show the position of a standardized production dataset $P_f$ of a first rolled material 2 in relation to four standardized production datasets $P_i$ of further rolled materials 2'. In a realistic application, the number M of input variables (corresponding to the production datasets $P_f$ and $P_i$, the further production datasets $F_f$ and $F_i$ and the metallurgical datasets $K_f$ and $K_i$ of the first rolled material and the further rolled materials 2 and 2') of the statistical data model 14 is greater than 2, for example 20 or 50. A representation of a realistic statistical data model 14 corresponding to FIG. 3 would accordingly comprise a mathematical map of an M-dimensional manifold to a curved M-dimensional manifold.

The mechanical property $S_{f,j}$ shown in FIG. 3 is a value (index j) from the second mechanical dataset $S_f$. The production parameters of the first rolled material 2 and the further rolled materials 2' are converted to dimensionless and standardized values $z_1$ and $z_2$ in accordance with the aforementioned formulae (13a) and (13b), for which the smallest and largest absolute values $x_{1,min}$, $x_{2,min}$, $x_{1,max}$, $x_{2,max}$ of each of the production parameters of all further rolled materials 2' are initially ascertained.

In FIG. 3, the two standardized production parameters $z_1$ and $z_2$ define a horizontal mathematical plane $e_1$ in which the position of the standardized production parameters $P_f$ of the first rolled material (star) and of production parameters $P_i$ of four further rolled materials 2' (vacant circles) is identified. From the relative position of the standardized production parameters in the plane $e_1$ in relation to each other it is possible for example to use formula (12) to ascertain a normalized distance value $d_{f,i}$ of the production dataset $P_f$ of the first rolled material 2 in relation to the respective production dataset $P_i$ of one of the further rolled materials 2', the value M=2 needing to be selected on the basis of the merely two input parameters $z_1$ and $z_2$ in formula (12) for the simplified example of FIG. 3. The connecting lines drawn in FIG. 3 between the standardized production parameters $P_f$ of the first rolled material 2 and the standardized production parameters $P_i$ of the further rolled materials 2' are an alternative to formula (12) in the form of the Euclidean norm within the plane $e_1$ for computation of a normalized distance value $d_{f,i}$ of the production dataset $P_f$ of the first rolled material 2 in relation to the respective production dataset $P_i$ of a further rolled material 2'.

The computation of the normalized distance values $d_{f,i}$ is followed by arithmetic averaging to ascertain the averaged normalized distance value $d_{f,m}$ of the production dataset $P_f$ of the first rolled material 2 in relation to the production datasets $P_i$ of the further rolled materials 2' from the n smallest normalized distance values $d_{f,i}$, the number n comprising 0.1 to 0.5 percent of the total number of further rolled materials 2'.

FIG. 3 furthermore shows, along the vertical axis, which runs normally to the plane $e_1$, the respective value, for each of the four sampling datasets $P_i$ shown for the further rolled materials 2', of a mechanical property with index j from the associated sampling dataset $B_i$ as a solid circle. These data points from the sampling datasets $B_i$ approximate a further, generally curved plane $e_2$, which is indicated in FIG. 3 by curved lines. In this context, "approximate" means that the data points from the sampling datasets $B_i$ are not necessarily situated exactly on the plane $e_2$, but may also be positioned at a short local normal distance therefrom, because the mathematical plane $e_2$ in the specific example of FIG. 3 is a regression plane. Within the framework of the predictive accuracy of the statistical data model 14, the regression plane $e_2$ represents an approximation to the data points of the sampling datasets $B_i$ of the further rolled materials 2', which have been used to train the statistical data model 14.

Along the vertical axis, FIG. 3 shows the value $S_{f,j}$ predicted by the statistical data model 14 for the mechanical property from the first mechanical dataset $S_f$ of the first rolled material 2 above the standardized production dataset $P_f$ of the first rolled material 2: this computed value replaces a physical sampling process for the first rolled material 2 and is usually 'close' to the plane $e_2$—this means that if the statistical data model 14 has a one hundred percent predictive accuracy, the data point $S_{f,j}$ is also an element of the plane $e_2$. However, since only a finite number of data of further rolled materials 2' are available for training the statistical data model 14 in the considered range of the production parameters $z_1$ and $z_2$, the value $S_{f,j}$ predicted by the statistical data model is—depending on the averaged normalized distance value $d_{f,m}$—located at a specific local normal distance from the plane $e_2$. In other words: in heavily populated ranges of the training data of the statistical data model 14 (resulting in a small value of $d_{f,m}$ for a first rolled material 2), in which a high number of training datasets is present, the value $S_{f,j}$ predicted by the statistical data model 14 is usually closer to the plane $e_2$ approximated by the body of the sampling data $B_i$ than in sparsely populated ranges of training data (large value of $d_{f,m}$).

FIG. 4 shows a data flow diagram for the method according to the invention for creating a hybrid model 10. The method according to the invention comprises three sequential steps S1' to S3'—i.e. steps to be carried out one after the other. Analogously to FIG. 2, the hybrid model 10 is shown using a broad line thickness and comprises production datasets $P_i$ of further rolled materials 2', a physical production model 12 with a set of metallurgical model parameters γ and a statistical data model 14. The further rolled materials 2' and rolled materials 2" form a first set $I_1$ and a second set $I_2$, respectively, and are each shown in FIG. 4 by a circle symbol with set braces. As in FIG. 2, the sequential steps of the method are represented by horizontal dashed lines; solid arrows again symbolize applicable data flows.

The rolled materials of the first and second quantities $I_1$, $I_2$ are each produced in the hot rolling mill 1, for which the hybrid model 10 is created, and then physically sampled, with the result that corresponding production data $P_i$ and sampling data $B_i$ are available. These data have been transmitted, for example as shown in FIG. 1, to the central evaluation unit 28, in which the hybrid model 10 is also created.

Also as in FIG. 2, in the present exemplary embodiment for creating a hybrid model 10 internal data structures, internal computation rules, relations between data and internal parameters are each realized as data or programming structures in the central computation unit 28, and so the method according to the invention for creating a hybrid model 10 can again be carried out as a program by the central computation unit 28.

The first step S1' involves at least one pass through the physical production model 12 taking place: this results in the first mechanical dataset, the further production dataset and the metallurgical dataset $C_i$, $F_i$, and $K_i$ being ascertained for each of the production datasets $P_i$ of the further rolled materials 2'.

Each ascertainment of these datasets is followed by a first measurement function $\varepsilon_1$ being used for component-by-component ascertainment, i.e. ascertainment for all individual mechanical properties in the further mechanical datasets $C_i$, of a measure of the deviation of the ascertained first mechanical datasets $C_i$ from the sampling datasets $B_i$ of the further rolled materials 2', the first measurement function $\varepsilon_1$ used, according to the present exemplary embodiment, being the expression of the aforementioned formulae (16) or (17). If the value of the first measurement function ($\varepsilon_1$) ascertained in this process for at least one mechanical property in the first mechanical datasets $C_i$ of the further rolled materials 2' is greater than a specified limit $\varepsilon_{max}$, the physical production model 12 is adapted by varying its metallurgical model parameters $\gamma$: this is shown in FIG. 4 by the dashed arrow of the first program branch identified by '1', the arrow tip of which protrudes into the rectangular symbol of the physical production model 12.

Another pass through the physical production model 12 then takes place, this also being referred to as a 'further iteration'. The first mechanical, further production and metallurgical datasets $C_i$, $F_i$ and $K_i$ are re-ascertained by solving the applicable equations of the physical production model 12—but in this case with the modified metallurgical model parameters $\gamma$—and then the first measurement function $\varepsilon_1$ is again used to perform a check on the deviation of the values of the newly ascertained first mechanical datasets $C_i$ from the corresponding values of the sampling datasets $B_i$.

If, after a pass through the physical production model 12, the value of the first measurement function $\varepsilon_1$ for all mechanical properties $C_i$,j (j denotes a single value within a mechanical dataset $C_i$) in the first mechanical datasets $C_i$ of the further rolled materials 2' is less than or equal to the limit $\varepsilon_{max}$, the production datasets $P_i$ of the further rolled materials 2', together with the corresponding further production and metallurgical datasets $F_i$, $K_i$ that were ascertained in the most recently performed iteration, are transferred to the statistical data model 14 as input variables and the corresponding sampling datasets $B_i$ are transferred to the statistical data model 14 as target variables. This case is represented in FIG. 4 by the arrows of the first program branch identified by '0'.

The second step S2' involves training the statistical data model (14) on the basis of the transferred input and target variables using a first machine learning method $V_1$ (shown in FIG. 4 by a square with rounded corners). Machine learning methods are known to those skilled in the art. Internal parameters of the statistical data model 14 are defined as appropriate: the statistical data model trained in this way is able to take a set of input parameters (for example the production parameters and further production parameters of a rolled material) and predict the corresponding mechanical properties without a sampling process. In the analogous example of FIG. 3, this means that the trained statistical data model 14 is able to map the plane $e_1$ (corresponding to the standardized production parameters $z_1$, $z_2$) to the—generally curved-plane $e_2$ for each mechanical property.

The subsequent third step S3' involves validating the trained statistical data model 14 on the basis of production datasets $P_i$ and sampling datasets $B_i$ of rolled materials 2" from a second set $I_2$. The second set $I_2$ is disjunct from the first set $I_1$, which means that none of the rolled materials whose production and sampling data $P_i$, $B_i$ have been used to train the statistical data model 14 are used for validating the trained statistical data model 14.

In the present exemplary embodiment of the method according to the invention, for validation, the production datasets $P_i$ of the rolled materials of the second set $I_2$ are supplied to the physical production model 12 with the metallurgical model parameters $\gamma$ that have been used in the most recently performed iteration: this is shown in FIG. 4 by the dashed arrow to the physical production model 12, which is also shown in dashed form, in the third method step S3'. A single pass through the physical production model 12 is used to ascertain the further production datasets $F_i$ and the metallurgical datasets $K_i$ for the rolled materials of the second set $I_2$, and these are then supplied together with the corresponding production datasets $P_i$ to the trained statistical data model 14 as input variables. Subsequently, the statistical data model 14 ascertains corresponding second mechanical datasets $S_i$ for the rolled materials of the second set $I_2$ from said input variables.

A second measurement function $\varepsilon_2$, which is provided in the present exemplary embodiment by the aforementioned formula (18), is used to ascertain a measure of a deviation of the individual variables in the mechanical datasets $S_i$ from the respective corresponding variables in the sampling datasets $B_i$ of the rolled materials of the second set $I_2$. If each value ascertained on the basis of the second measurement function $\varepsilon_2$ is less than or equal to a specified limit $\varepsilon_{max}$, the statistical data model 14 with the internal parameters determined during training is transferred to the hybrid model 10 (shown in FIG. 4 by the arrow of the second program branch identified by '0'). The limit $\varepsilon_{max}$ may be the same value as was used for adapting the physical production model in the first method step S1'.

If one of the values ascertained on the basis of the second measurement function $\varepsilon_2$ is greater than the specified limit $\varepsilon_{max}$, the statistical data model is adapted further by, in the present exemplary embodiment of the method according to the invention, training the statistical data model 14 (or each partial data model) on the basis of a second machine learning method $V_2$, which is different from the first machine learning method $V_1$, and the second method step S2' is repeated: this case is indicated in FIG. 4 by the dashed arrow of the second program branch identified by '1'. In contrast to the aforementioned 'first' machine learning method, the invention involves the 'second' machine learning method being employed only in the event of unsuccessful validation of the statistical data model 14 (or one of the partial data models).

Alternatively or in addition, in the event of unsuccessful validation (i.e. $\varepsilon_2 \geq \varepsilon_{max}$), the first and second quantities $I_1$, $I_2$ of rolled materials whose production and sampling data $P_i$, $B_i$ are used to train and validate the statistical data model 14 can also be modified (not shown in FIG. 4). In turn, one and the same second machine learning method $V_2$ can be used for validating each of the individual partial data models, said second machine learning method merely being different from the first machine learning method $V_1$ of the respective partial data model. Alternatively, the second machine learning methods $V_2$ for validating the individual partial data models may also differ from each other.

LIST OF REFERENCE SIGNS 1 rolling mill, hot rolling mill
2, 2', 2" rolled material
3 heating furnace
4 roughing line
5 cropping shear
6 temperature measuring device, pyrometer
7 finishing rolling line 8 cooling section
9 sampling device
10 hybrid model
12 physical production model
14 statistical data model
20, 20', 20" rolled material section
26 coiling device
27 installation controller
28 central evaluation unit
$a_k$ morphological characteristic
$A_1 \ldots A_{13}$ rolling mill section
$B_i$ sampling dataset
$B_{i,j}$ value from the sampling dataset
$C_f$, $C_i$ first mechanical dataset
$C_{f,j}$, $C_{i,j}$ individual value in first mechanical dataset
$d_{f,i}$ normalized distance value
$d_{f,m}$ averaged normalized distance value
$\delta_j$ function parameters
$e_1$, $e_2$ plane
$\varepsilon_1$, $\varepsilon_2$ measurement function
$\varepsilon_{max}$ limit
$F_f$, $F_i$ further production dataset
$\gamma$ metallurgical model parameters
$I_1$, $I_2$ set
$J_f$ mechanical properties
$J_{f,j}$ single mechanical property
$K_f$, $K_i$ metallurgical dataset
$\lambda_j$ function parameters
$p_k$ phase fraction
$P_f$, $P_i$ production dataset
$q_z$ cooling rate
$Q_1 \ldots Q_4$ cooling device
$R_1 \ldots R_5$ roll stand
S1 ... S5 method step
S1' ... S3' method step
$S_f$, $S_i$ second mechanical dataset
$S_{f,j}$ value from the second mechanical dataset
$T_z$ temperature value
$V_1$, $V_2$ machine learning method
$w_i$ weighting factor
$w_j(d_{f,m})$ weighting function
$x_{k,f}$, $x_{k,i}$ component in production dataset
$x_{k,min}$ minimum value for component k
$x_{k,max}$ maximum value for component
$z_{k,f}$, $z_{k,i}$ standardized value in production dataset

The invention claimed is:

1. A method for determining mechanical properties of a first rolled material, produced in a rolling mill, using a hybrid model, based on a production dataset of the first rolled material, the hybrid model comprising:
production datasets of further rolled materials, produced in the rolling mill, from a first set that each have available corresponding sampling datasets, comprising the mechanical properties of the further rolled materials ascertained by a sampling device after production in the rolling mill;
a physical production model comprising a set of metallurgical model parameters, for ascertaining:
a first mechanical dataset, comprising the mechanical properties of the first rolled material after production in the rolling mill,
a further production dataset, comprising further production data of the first rolled material during production in the rolling mill,
and a metallurgical dataset, comprising metallurgical properties of the first rolled material during production in the rolling mill, and
a trained and validated statistical data model for ascertaining a second mechanical dataset, comprising the mechanical properties of the first rolled material after production in the rolling mill;
wherein the method comprises a first, a second, a third and a fourth step;
wherein the first step involves ascertaining the first mechanical dataset, the further production dataset and the metallurgical dataset of the first rolled material from the production dataset of the first rolled material via the physical production model;
wherein the second step involves ascertaining the second mechanical dataset of the first rolled material from the production dataset, the further production dataset and the metallurgical dataset of the first rolled material via the statistical data model;
wherein the third step involves determining for the production dataset of the first rolled material an averaged normalized distance value in relation to a number of production datasets of the further rolled materials; and
wherein the fourth step involves using the averaged normalized distance value to ascertain the mechanical properties of the first rolled material as a weighted average from the first and second mechanical datasets, the quotients of the mutually corresponding values of the second and first mechanical datasets being weighted in proportion to the averaged normalized distance value.

2. The method as claimed in claim 1, wherein the mechanical properties of the first rolled material comprise at least one of a tensile strength, a yield strength, and an elongation at break.

3. The method as claimed in claim 1, wherein:
the averaged normalized distance value is formed from normalized distance values of the production dataset of the first rolled material in relation to a respective production dataset of one of the further rolled materials; and
the number of production datasets comprises 0.1 to 0.5% of the training datasets of the statistical data model.

4. The method as claimed in claim 1, wherein the mechanical properties of the first rolled material are ascertained for at least one rolled material section of the first rolled material.

5. The method as claimed in claim 4, wherein:
the rolling mill comprises roll stands, cooling devices, rolling mill sections, and at least one coiling device;
the production datasets of the first rolled material and the further rolled materials each comprise at least one of the following manipulated or measured variables for at least one rolled material section of the first rolled material and the further rolled materials:
one or more foreign element fractions in the rolled material section,
at least one of a thickness and a width of the rolled material section before entering a first roll stand,
at least one of a thickness and a width of the rolled material section after exiting a last roll stand,
at least one temperature of the rolled material section recorded by a measuring arrangement,
at least one roll gap value of one of the roll stands when the rolled material section passes through the applicable roll stand,
at least one coolant stream emitted by one of the cooling devices when the rolled material section passes through the operating range of the applicable cooling device, or at least one speed of the rolled material section in one of the rolling mill sections.

6. The method as claimed in claim 4, wherein the further production dataset for at least one rolled material section of the first rolled material comprises at least one of:
   at least one modeled cooling rate of the rolled material section when passing through at least one of the rolling mill sections of the rolling mill; and
   at least one modeled temperature value of the rolled material section when passing through the at least one of the rolling mill sections of the rolling mill.

7. The method as claimed in claim 4, wherein the metallurgical properties of the metallurgical dataset comprise at least one of phase fractions and morphological characteristics of different metallurgical phases of at least one rolled material section of the first rolled material.

8. The method as claimed in claim 4, wherein a fifth step involves subjecting the ascertained mechanical properties of the first rolled material to a cooling correction in which carbide and nitride precipitations in the first rolled material are taken into account during cooling after production in the rolling mill.

9. A method for creating a hybrid model for determining mechanical properties of a first rolled material produced in a rolling mill, the hybrid model comprising:
   production datasets of further rolled materials, produced in the rolling mill, from a first set that each have available corresponding sampling datasets, comprising the mechanical properties of the further rolled materials ascertained by a sampling device after production in the rolling mill;
   a physical production model having a set of metallurgical model parameters for ascertaining:
      a first mechanical dataset, comprising the mechanical properties after production in the rolling mill,
      a further production dataset, comprising further production data during production in the rolling mill,
      and a metallurgical dataset, comprising metallurgical properties during production in the rolling mill,
   for each of the further rolled materials; and
   a statistical data model for ascertaining a second mechanical dataset, comprising the mechanical properties after production in the rolling mill, for each of the further rolled materials;
   wherein one or more consecutive iterations of a first step involve using the physical production model to ascertain for each of the production datasets of the further rolled materials the corresponding first mechanical dataset and further production and metallurgical datasets;
   wherein each iteration is followed by a first measurement function being used for component-by-component ascertainment, for all first mechanical datasets ascertained in the most recently performed iteration, of a measure of the deviation from the corresponding sampling datasets of the further rolled materials;
   wherein if the value of the first measurement function for at least one mechanical property in the first mechanical datasets of the further rolled materials is greater than a limit, the metallurgical model parameters are varied and, in a further iteration, the first mechanical datasets, the further production datasets and the metallurgical datasets of the further rolled materials are re-ascertained based on the physical production model with the modified metallurgical model parameters;
   wherein if the value of the first measurement function for all mechanical properties in the first mechanical datasets of the further rolled materials is less than or equal to the limit, the production datasets together with the further production and metallurgical datasets of the further rolled materials ascertained in the most recently performed iteration are transferred to the statistical data model as input variables and the corresponding sampling datasets are transferred to the statistical data model as target variables;
   wherein a second step involves training the statistical data model based on the transferred input and target variables using a first machine learning method; and
   wherein a third step involves validating the trained statistical data model based on production datasets and sampling datasets of rolled materials from a second set, which is disjunct from the first set, by supplying the further production datasets and metallurgical datasets ascertained for the rolled materials of the second set by the physical production model, together with the production datasets of the rolled materials of the second set, to the trained statistical data model as input variables and ascertaining corresponding second mechanical datasets by the trained statistical data model and ascertaining component-by-component-wise a measure of a deviation from the corresponding sampling datasets for said second mechanical datasets based on a second measurement function.

10. The method as claimed in claim 9, wherein the mechanical properties of the first rolled material and the sampling datasets, the first and the second mechanical datasets of the further rolled materials each comprise at least one of a tensile strength, a yield strength, and an elongation at break.

11. The method as claimed in claim 9, wherein the first step is preceded by the sampling dataset from each of the further rolled materials that corresponds to the production dataset being transformed to a normalized sample geometry according to Oliver's formula.

12. The method as claimed in claim 9, wherein the mechanical properties of the first rolled material and the first and second mechanical datasets of the further rolled materials are each ascertained for at least one rolled material section of the first rolled material and the further rolled materials.

13. The method as claimed in claim 12, wherein:
   the rolling mill has roll stands, cooling devices, rolling mill sections and at least one coiling device; and
   the production datasets of the first rolled material and the further rolled materials each comprise at least one of the following manipulated or measured variables for at least one rolled material section of the first rolled material and the further rolled materials:
      one or more foreign element fractions in the rolled material section,
      at least one of a thickness and a width of the rolled material section before entering a first roll stand of the rolling mill,
      at least one of a thickness and a width of the rolled material section after exiting a last roll stand of the rolling mill,
      at least one temperature of the rolled material section recorded by a measuring arrangement,
      at least one roll gap value of one of the roll stands when the rolled material section passes through the respective roll stand, at least one coolant stream emitted by one of the cooling devices when the rolled material section passes through the operating range of the respective cooling device, or at least one speed of the rolled material section in one of the rolling mill sections.

14. The method as claimed in claim 12, wherein the further production dataset for at least one rolled material section of each of the further rolled materials comprises at least one of:

at least one modeled cooling rate of the rolled material section when passing through at least one of the rolling mill sections of the rolling mill; and at least one modeled temperature value of the rolled material section when passing through the at least one of the rolling mill sections of the rolling mill.

15. The method as claimed in claim 12, wherein the datasets of the further rolled materials comprise at least one of phase fractions and morphological characteristics of different metallurgical phases of at least one rolled material section of each of the further rolled materials.

* * * * *